(12) United States Patent
Coe et al.

(10) Patent No.: US 12,380,976 B2
(45) Date of Patent: *Aug. 5, 2025

(54) CLINICAL LABORATORY-BASED DISEASE MANAGEMENT PROGRAM, WITH AUTOMATED PATIENT-SPECIFIC TREATMENT ADVICE

(71) Applicant: Laboratory Corporation of America Holdings, Burlington, NC (US)

(72) Inventors: Fredric L Coe, Chicago, IL (US); Brian J. Coe, Chicago, IL (US); John R. Asplin, Chicago, IL (US); Enno de Vries, Tower Lakes, IL (US); Elaine Worcester, Chicago, IL (US)

(73) Assignee: Laboratory Corporation of America Holdings, Burlington, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/439,707

(22) Filed: Feb. 12, 2024

(65) Prior Publication Data

US 2024/0347155 A1 Oct. 17, 2024

Related U.S. Application Data

(63) Continuation of application No. 17/516,928, filed on Nov. 2, 2021, now Pat. No. 11,901,054, which is a
(Continued)

(51) Int. Cl.
*G06Q 10/00* (2023.01)
*A61B 5/00* (2006.01)
(Continued)

(52) U.S. Cl.
CPC .............. *G16H 15/00* (2018.01); *G16H 10/20* (2018.01); *G16H 40/20* (2018.01); *G16H 70/20* (2018.01); *G16H 10/40* (2018.01); *G16H 50/20* (2018.01)

(58) Field of Classification Search
CPC ........ G16H 15/00; G16H 10/20; G16H 40/20; G16H 70/20; G16H 10/40; G16H 50/20
See application file for complete search history.

(56) References Cited

U.S. PATENT DOCUMENTS 6,208,974 B1 3/2001 Campbell et al.
7,306,562 B1 12/2007 Baykal
(Continued)

OTHER PUBLICATIONS

U.S. Appl. No. 12/535,287, "Final Office Action", dated Jul. 31, 2012, 12 pages.
(Continued)

*Primary Examiner* — Maroun P Kanaan
(74) *Attorney, Agent, or Firm* — Kilpatrick Townsend & Stockton LLP

(57) ABSTRACT

A method is provided, the method including receiving a test result data, wherein said test result data represents a result of a test on a physical specimen, associating said test result data with a standard-of-care data, wherein said standard-of-care data represents a recommended course of action for the condition represented by the test result data, and transforming said specimen data and said standard-of-care data into a human-readable form. A system including a processor is provided, a software adapted to be executed on said processor, said software comprising instructions for receiving a test result data, wherein said test result data represents a result of a test on a physical specimen, associating said test result data with a standard-of-care data, wherein said standard-of-care data represents a recommended course of action for the condition represented by the test result data, and transforming said specimen data and said standard-of-care data into a human-readable form.

20 Claims, 31 Drawing Sheets

Related U.S. Application Data continuation of application No. 16/403,915, filed on May 6, 2019, now Pat. No. 11,195,603, which is a continuation of application No. 13/755,361, filed on Jan. 31, 2013, now Pat. No. 10,290,369, which is a continuation of application No. 12/535,287, filed on Aug. 4, 2009, now abandoned.

(60) Provisional application No. 61/086,023, filed on Aug. 4, 2008.

(51) Int. Cl.
| | | |
|---|---|---|
| *G16H 10/20* | (2018.01) | |
| *G16H 15/00* | (2018.01) | |
| *G16H 40/20* | (2018.01) | |
| *G16H 70/20* | (2018.01) | |
| G16H 10/40 | (2018.01) | |
| G16H 50/20 | (2018.01) | |

(56) References Cited

U.S. PATENT DOCUMENTS

| | | | |
|---|---|---|---|
| 7,493,264 B1* | 2/2009 | Kelly | G16H 15/00 600/595 |
| 10,290,369 B2 | 5/2019 | Coe et al. | |
| 11,195,603 B2 | 12/2021 | Coe et al. | |
| 11,901,054 B2 | 2/2024 | Coe et al. | |
| 2001/0013006 A1 | 8/2001 | Brown | |
| 2003/0135393 A1 | 7/2003 | Burgess | |
| 2004/0030586 A1 | 2/2004 | Cucchiara et al. | |
| 2004/0034288 A1 | 2/2004 | Hennessy et al. | |
| 2004/0078222 A1 | 4/2004 | Khan et al. | |
| 2004/0103001 A1 | 5/2004 | Mazar et al. | |
| 2005/0010444 A1 | 1/2005 | Iliff | |
| 2005/0261558 A1 | 11/2005 | Eaton et al. | |
| 2006/0064250 A1 | 3/2006 | Goldstein | |
| 2007/0033075 A1 | 2/2007 | Hoffman et al. | |
| 2007/0034213 A1 | 2/2007 | Poisner | |
| 2007/0122824 A1 | 5/2007 | Tucker et al. | |
| 2007/0168373 A1 | 7/2007 | Dettinger et al. | |
| 2007/0192134 A1* | 8/2007 | Littenberg | G16H 70/20 600/300 |
| 2008/0065422 A1 | 3/2008 | Weber | |
| 2009/0119130 A1 | 5/2009 | Kimmel et al. | |
| 2010/0076787 A1 | 3/2010 | Naylor et al. | |
| 2010/0280395 A1 | 11/2010 | Lin | |
| 2014/0039909 A1 | 2/2014 | Coe et al. | |

OTHER PUBLICATIONS

U.S. Appl. No. 12/535,287, "Non-Final Office Action", dated Nov. 29, 2011, 13 pages.
U.S. Appl. No. 13/755,361 , "Final Office Action", Apr. 28, 2016, 25 pages.
U.S. Appl. No. 13/755,361, "Final Office Action", dated Dec. 3, 2014, 17 pages.
U.S. Appl. No. 13/755,361, "Final Office Action", dated Jun. 7, 2018, 16 pages.
U.S. Appl. No. 13/755,361, "Non Final Office Action", dated Aug. 13, 2015, 19 pages.
U.S. Appl. No. 13/755,361, "Non-Final Office Action", dated Aug. 11, 2017, 16 pages.
U.S. Appl. No. 13/755,361, "Non-Final Office Action", dated Aug. 12, 2014, 11 pages.
U.S. Appl. No. 13/755,361 , "Notice of Allowance", dated Dec. 18, 2018, 8 pages.
U.S. Appl. No. 16/403,915 , "Advisory Action", dated Apr. 12, 2021, 5 pages.
U.S. Appl. No. 16/403,915, "Final Office Action", dated Feb. 17, 2021, 16 pages.
U.S. Appl. No. 16/403,915, "Non-Final Office Action", dated May 12, 2021, 8 pages.
U.S. Appl. No. 16/403,915, "Non-Final Office Action", dated Oct. 6, 2020, 15 pages.
U.S. Appl. No. 16/403,915, "Notice of Allowance", dated Aug. 5, 2021, 5 pages.
U.S. Appl. No. 17/516,928, "Non-Final Office Action", dated Apr. 13, 2023, 15 pages.
U.S. Appl. No. 17/516,928, "Notice of Allowance", dated Oct. 4, 2023, 11 pages.
PCT/US09/52692, "International Search Report and Written Opinion", dated Sep. 24, 2009, 9 pages.

* cited by examiner

LitholinkCKD

CKD Test Request Form

Physician Instructions:
① Fax Litholink at 312 361 7939   ② Hand to patient *(patient will take to draw center)*

Patient Information:

Patient Last Name    First Name    MI

*lbs*    *kg*
Weight    Blood Pressure

Self-reported Race: ☐ African-American  ☐ Asian  ☐ Caucasian  ☐ Hispanic  ☐ Other

Treatments:

|  | Yes | No |  | Yes | No |
|---|---|---|---|---|---|
| Phosphate Binder | ☐ | ☐ | ESA* | ☐ | ☐ |
| Calcium Based Binder | ☐ | ☐ | Iron | ☐ | ☐ |
| Active Vitamin D | ☐ | ☐ | Alkali | ☐ | ☐ |
| Vitamin D | ☐ | ☐ | ACEI or ARB | ☐ | ☐ |
| Statin | ☐ | ☐ | Low Phosphate Diet | ☐ | ☐ |
| Fibrate | ☐ | ☐ | Diuretic | ☐ | ☐ |
| Niacin | ☐ | ☐ |  |  |  |

Medical Information:

Yes  No
Diabetes  ☐  ☐

Requested Tests: *(panel description on reverse)*

Diagnosis
☐ CKD Stage _____ ☐ CKD Uspecified
☐ Other _____

Blood
☐ A. CBC w/o differential
☐ B. CBC w/o differential + Retic Count
☐ C. Renal Panel
☐ D. Renal Panel + Intact PTH
☐ E. 25 Hydroxy Vitamin D
☐ F. Creatine Kinase
☐ G. ALT + AST

*CKD co-morbidities*   *Diagnosis*
☐ H. Fe/TIBC  _____
☐ I. Ferritin  _____
☐ J. Liquid Panel*  _____
☐ K. Hemoglobin A1C  _____

Spot Urine
☐ L. Albumin: Creatinine ratio
☐ M. Total Protein: Creatinine ratio

*w/ billed Direct LDL only if triglycerides ≥ 400 mg/dL*

☐ See LabCorp order sheet for additional orders

Physician Name    Physician Signature    Date

*This program is intended for patients who have been diagnosed with Chronic Kidney Disease.*

Phlebotomist Information:
*See shipping box provided by patient for supplies and instructions.*

Fasting  ☐ Yes ☐ No    X-Code

Blood Draw Date    Blood Draw Time    Spot Urine Collection Date    Spot Urine Collection Time

Figure 1A

Panel Descriptions and Required Tubes

Blood

| PANEL/TEST | MEASURED | REQUIRED TUBE | CPT CODE |
|---|---|---|---|
| CBC w/o differential | Hemoglobin, White Blood Count, Red Blood Count, Platelet Count, MCV Calculated: *Hematocrit MCH, MCHC, RDW* | Lavender Top (EDTA) | 85027 |
| CBC w/o differential + Retic Count | CBC w/o differential Reticulocyte Count Calculated: *Absolute Reticulocyte Count* | Lavender Top (EDTA) | 85027<br>85045 |
| Fe/TIBC (TSAT – Transferrin Saturation) | Iron UIBC Calculated: *TIBC, TSAT* | Gold Top (SST) | 83540<br>83550 |
| Ferritin | Ferritin | White Top (PPT) | 82728 |
| Lipid Panel\* <br>*\*w/billed Direct LDL only if triglycerides ≥ 400 mg/dL* | Total Cholesterol, HDL, Triglycerides, Calculated: LDL (if triglycerides < 400mg/dL), VLDL, non-HDL, Direct LDL (if triglycerides ≥ 400mg/dL) | Gold Top (SST) | 80061<br><br>83721 |
| Renal Panel | Sodium, Potassium, $CO_2$ Chloride, BUN, Creatinine, Glucose, Calcium, Phosphorus, Albumin Calculated: *eGFR, Corrected Calcium* | Gold Top (SST) | 80069 |
| Renal Panel + Intact PTH | Intact PTH<br>Renal Panel | White Top (PPT)<br>Gold Top (SST) | 83970<br>80069 |
| Hemoglobin A1C | Hemoglobin A1C | Lavender Top (EDTA) | 83036 |
| 25 Hydroxy Vitamin D | 25 Hydroxy Vitamin D | White Top (PPT) | 82306 |
| Creatine Kinase | Creatine Kinase | Gold Top (SST) | 82550 |
| ALT + AST | ALT<br>AST | Gold Top (SST) | 84460<br>84450 |

Spot Urine

| PANEL/TEST | MEASURED | | CPT CODE |
|---|---|---|---|
| Albumin: Creatinine Ratio | Albumin, urine<br>Creatinine, urine | | 82043<br>82570 |
| Total Protein: Creatinine Ratio | Total protein, urine<br>Creatinine, urine | | 84156<br>82570 |

Figure 1B

LitholinkCKD

| Patient Results Report | | |
|---|---|---|
| PATIENT<br>Sample, Patient | DATE OF BIRTH<br>06/03/1951 | PRACTICE<br>Sample Nephrology Practice |

Physician Name
Hospital / Practice Name
Primary Address Line
Secondary Address Line
City Name, State 012345

Medical Director's Notes

Laboratory test values flagged with an asterisk (*) within this report refer to the following commentary from our physicians and quality assurance staff. Please feel free to call us at 800 338 4333 with questions you may have regarding this information.

| SAMPLE ID | TEST COMPLETION DATE | ITEM | RELATED NOTES |
|---|---|---|---|
| 089979 | 12/04/04 | ??? | Lorem Ipsom dolar sit amet consectatur |

*John Asplin, MD*
*Medical Director*

Beta Testing Comments & Questions

*Fax to 312 243 3297 or email to sdonahue@litholink.com*

Figure 3

LitholinkCKD

Patient Results Report

| PATIENT | DATE OF BIRTH | PRACTICE |
|---|---|---|
| Sample, Patient | 06/03/1951 | Sample Nephrology Practice |

Summary eGFR

510 — The chart below shows summary eGFR data over time, from the oldest recorded test to the most recent. The ten most recent tests are indicated within brackets. Data for the tests is reflected in this report on the following pages.

520 — Annualized rate of decline (all values) is -1.010 ml/min/year, p= 0.000. Estimated interval to CKD 5 (using most recent eGFR values) is [CKDOnset] months (67% CI = [CKDOnsetMin]-[CKDOnset] months). Without knowledge of present blood pressure medication we cannot interpret blood pressure values nor make recommendations. Your office reports ACEI/ARB treatment is used. Your office reports no information about Diuretic.

| GENDER | ETHNICITY | LAST eGFR | LAST CKD STAGE | CURRENT CKD STAGE |
|---|---|---|---|---|
| M | NAA | 11 | 5 | 5 |

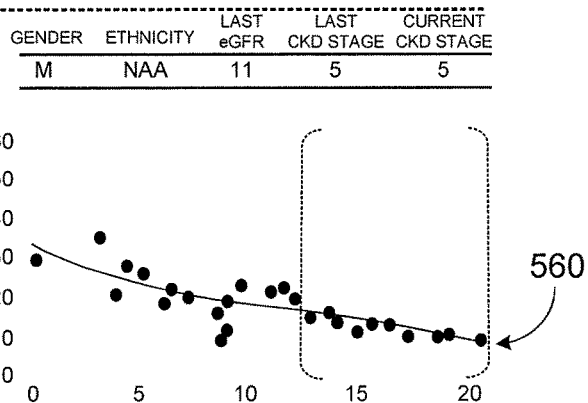

560

530 — (TREATMENT OPTIONS) Lifestyle should include sodium intake less than 3000 mg/d, exercise (30 minutes 5 times a week), less than three alcoholic drinks per day, low dose baby aspirin (81 mg/d), and smoking cessation. Consider decreasing ACEI/ARB dose.

(FOLLOW UP OPTIONS) Spot Urine Panel (Protein or Albumin [preferred]) is due now; Blood Pressure Measurement and Renal Panel within 1 month.

eGFR Test Results

590

| TEST DATE | SCr | eGFR | Protein/Cr (mg/g) | Alb/Cr (mg/g) | HB A1c | SYSTOLIC | DIASTOLIC | ACE/ARB | DIABETES |
|---|---|---|---|---|---|---|---|---|---|
| 01/08/08 | 4.44 | 10 | 1190 | | | | | | |
| 11/26/07 | 4.15 | 11 | | | | 142 | 60 | | |
| 11/07/07 | 4.1 | 12 | 1283 | | | | | | |
| 10/02/07 | 3.9 | 13 | | | | 144 | 64 | | |
| 09/04/07 | 3.5 | 14 | 1627 | | | | | | |
| 08/09/07 | 3.4 | 15 | | | | | | | |
| 07/23/07 | 3.7 | 13 | 1140 | | 9.7 | | | | |
| 06/25/07 | 3.3 | 15 | | | | | | | |
| 06/14/07 | 2.9 | 18 | | | | | | | |
| 05/21/07 | 3.1 | 16 | | | | | | | |

Figure 5

LitholinkCKD

| Patient Results Report | | |
|---|---|---|
| PATIENT<br>Sample, Patient | DATE OF BIRTH<br>06/03/1951 | PRACTICE<br>Sample Nephrology Practice |

Bone & Mineral

610 Parathyroid Hormone (Intact) is above goal and has risen, was 94 and now is 132 pg/mL. Phosphorus is above goal and has risen 4.7 and now is 5.6 mg/dl. Corrected Calcium is at goal and has not changed significantly, was 9.0 and now is 9.3 mg/dl. Potassium is above goal and has risen, was 4.4 and now is 5.5 mmol/l. Carbon Dioxide is below goal and has not changed significantly, was 19 and now is 20 mmol/l. Vitamin D is adequate (was 40 now is 32 pg/mL). Your office reports low phosphate diet and vitamin D treatments are used and phosphate binders, active vitamin D analog, and alkali treatments are not being used. 640

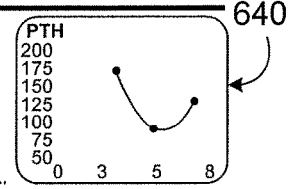

620 (TREATMENT OPTIONS) Maintain vitamin D stores with an OTC vitamin D containing multivitamin. As much as 1000-2000 units daily may be required. If in effect, discontinue high dose ergocalciferol/cholecalciferol therapy. Continue low phosphorus diet. Confirm adherence to low phosphate diet. Begin phosphate binder. Typical starting dosage is one pill with each substantial meal based on clinical evaluation of diet. Calcium based binder may be preferable. Maximum dose of elemental calcium is 1.5 g/day. Hyperkalemia and low C02 may reflect Type 4 renal tubular acidosis. Hyperkalemia precludes use of potassium alkali; use sodium alkali.

630 Consider sodium bicarbonate 16 – 24 mEq/d. Potassium sparing diuretics, ACE inhibitor, ARB, or excessive potassium intake are possible causes of hyperkalemia.

(FOLLOW UP OPTIONS) Renal Panel within 1 month; PTH within 3 months; 25-D within 12 months.

Lipids

LDL is above goal and has not changed significantly, was 135 and now is 142 mg/dL. Triglyceride is at goal and has fallen, was 278 and now is 192 mg/dL. Non-HDL Cholesterol is above goal and has fallen, was 191 and now is 180 mg/dL. Your office reports statin treatment is used and fibrate treatment is not being used. Your office reports no information about niacin.

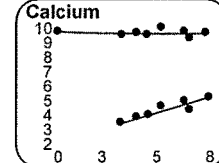

(TREATMENT OPTIONS) Therapeutic lifestyle changes are always recommended for dyslipidemia (diet, exercise, weight management). Increase statin dose if not already maximal [dosing table]. Consider nicotinic acid if not already in use. Ezetimibe is an alternative therapy for high LDL [dosing table].

(FOLLOW UP OPTIONS) Fasting Lipid Panel within 3 months.

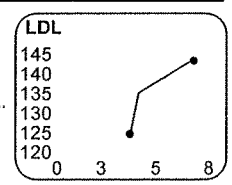

Anemia

Hemoglobin is low and has not changed significantly, was 11.8 and now is 11.7 g/dL. TSAT is below goal and has fallen, was 65 and now is 9%. Ferritin is below goal and has not changed significantly, was 22 and now is 7 ng/ml. Your office reports ESA and iron treatments are not being used.

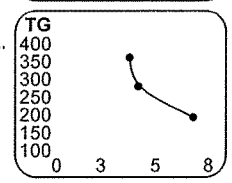

(TREATMENT OPTIONS) Begin oral iron supplements or IV iron [need dosing]. Falling TSAT suggests consumption of iron stores or blood loss.

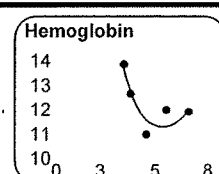

(FOLLOW UP OPTIONS) CBC, Ferritin, and Fe/TIBC (TSAT) within 3 months.

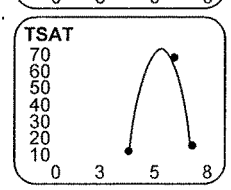

Figure 6

LitholinkCKD

Patient Results Report

| PATIENT | DATE OF BIRTH | PRACTICE |
|---|---|---|
| Sample, Patient | 06/03/1951 | Sample Nephrology Practice |

Test Results & Treatments

Bone & Mineral — 710 / 720

| TEST DATE | PTH | P | Corr Ca | $CO^2$ | K | 25-0 | LPD | PB | $C_2$PB | 1,250 | D | ALKALI |
|---|---|---|---|---|---|---|---|---|---|---|---|---|
| 01/08/08 | 132 | 5.6 | 9.34 | 20 | 5.5 | 32 | Yes | No | No | No | Yes | No |
| 11/15/06 |  | 4.7 | 9.02 | 19 | 4.4 |  | Yes | No | No | No | Yes | No |
| 11/06/06 |  | 5.1 | 9.40 | 20 | 5.4 |  | Yes | No | No | No | Yes | No |
| 10/05/06 | 94 | 4.8 | 9.58 | 23 | 5.1 | 40 | Yes | No | No | No | Yes | No |
| 09/15/06 |  | 4.3 | 9.22 | 23 | 4.5 |  | No | No | No | No | Yes | No |
| 09/01/06 |  | 4.1 | 9.20 | 21 | 4.3 |  | No | No | No | No | Yes | No |
| 08/11/06 | 175 | 3.9 | 9.20 | 24 | 4.3 | 24 | No | No | No | No | No | No |
| 05/16/06 |  |  | 9.46 | 29 | 4.4 |  | No | No | No | No | No | No |

Lipids

| TEST DATE | LDL | TG | NON-MDL | CHOL | MDL | STATIN | FIBRATE | NIACIN | FASTING |
|---|---|---|---|---|---|---|---|---|---|
| 12/05/06 | 142 | 192 | 180 | 223 | 43 | Yes | No | ? | ? |
| 09/15/06 | 135 | 278 | 191 | 234 | 43 | Yes | No | ? | ? |
| 09/01/06 | 125 | 356 | 196 | 235 | 39 | Yes | No | ? | ? |

Anemia

| TEST DATE | MB | TSAT | FERRITIN | IRON | ESA |
|---|---|---|---|---|---|
| 12/05/06 | 11.7 | 9 | 7 | No | No |
| 11/06/06 | 11.8 | 65.2 | 22 | No | No |
| 10/05/06 | 10.9 |  |  | No | No |
| 09/11/06 | 12.4 |  |  | No | No |
| 09/01/06 | 13.5 | 6.2 | 11 | No | No |

Figure 7

LitholinkCKD

Patient Results Report

| PATIENT | DATE OF BIRTH | CKD STAGE | DATE OF SERVICE | PHYSICIAN |
|---|---|---|---|---|
| Patient 2, Sample | 04/15/1960 | 3 | 05/17/2006 | Physician, Sample |

Sample Physician MD
Medical Associates
10 Main Street
Suite 150
Chicago, IL 60612

Laboratory Director's Notes

Mitchell S. Laks, Ph.D.
*Laboratory Director*

LitholinkCKD

Patient Results Report — 910

| PATIENT | DATE OF BIRTH | CKD STAGE | DATE OF SERVICE | PHYSICIAN |
|---|---|---|---|---|
| Patient 2, Sample | 04/15/1960 | 3 | 05/17/2006 | Physician, Sample |

920 Current Laboratory Results

ANALYTE  RESULT UNIT  REFERENCE INTERVAL  ( LOW RESULT )( REF. INT. )( HIGH RESULT )

BLOOD DRAW DATE: 05/17/2006  DRAWTIME: 09:30  FASTING: YES

Renal Panel

| Analyte | Result Unit | Reference Interval | Indicator |
|---|---|---|---|
| Glucose | 136 mg/dl | 86 - 99 | 136 (high) |
| BUN | 26 mg/dl | 5 - 26 | 26 |
| Creatinine | 1.60 mg/dl | 0.76 - 1.27 | 1.60 (high) |
| Sodium | 135 mmol/l | 135 - 145 | 135 |
| Potassium | 4.3 mmol/l | 3.5 - 5.2 | 4.3 |
| Chloride | 101 mmol/l | 97 - 108 | 101 |
| Carbon Dioxide | 25 mmol/l | 20 - 32 | 25 |
| Albumin | 4.3 g/dl | 3.5 - 5.5 | 4.3 |
| Calcium | 9.3 mg/dl | 8.5 - 10.6 | 9.3 |
| Corrected Calcium | 9.1 mg/dl | 8.5 - 10.6 | 9.1 |
| Phosphorus | 4.1 mg/dl | 2.5 - 4.5 | 4.1 |
| Anion Gap | 9 mmol/l | 8 - 14 | 9 |
| Estimated GFR | 47 ml/min/1.73mE2 | > 59 | 47 (low) |

Salicylate-containing medications can falsely elevate chloride results using the Roche Integra methodology. Albumin testing performed on the Roche Integra 800 using the Gen.2 assay.

Intact PTH

| Intact PTH | 89 pg/ml | 15 - 65 | 89 (high) |
|---|---|---|---|

PTH testing performed using the PTH assay on the Roche Elecsys 2010.

25 Hydroxy Vitamin D

| 25-Hydroxy Vitamin D | 9.0 ng/ml | 32.0 - 100.0 | 9.0 (low) |
|---|---|---|---|

Vitamin D testing performing using the 25 OH Vitamin D Total Assay on the DiaSorin Liaison®.

CBC w/o differential

| White Blood Count | 5.8 x10E3/ul | 4.0 - 10.5 | 5.8 |
|---|---|---|---|
| Red Blood Count | 4.20 x10E6/ul | 4.10 - 5.60 | 4.20 |
| Hemoglobin | 12.2 g/dl | 12.5 - 17.0 | 12.2 (low) |
| Hematocrit | 35.4 % | 36.0 - 50.0 | 35.4 (low) |
| MCV | 83 fl | 80 - 98 | 83 |
| MCH | 32.0 pg | 27.0 - 34.0 | 32.0 |
| MCHC | 35.0 g/dl | 32.0 - 36.0 | 35.0 |
| RDW | 12.4 % | 11.7 - 15.0 | 12.4 |
| Platelet Count | 296 x10E3/ul | 140 - 415 | 296 |

Fe/TIBC

| Iron | 108 ug/dl | 40 - 155 | 108 |
|---|---|---|---|
| UIBC | 154 ug/dl | 150 - 375 | 154 |
| TIBC | 262 ug/dl | 250 - 450 | 262 |
| TSAT | 21.0 % | 15.0 - 55.0 | 21.0 |

Ferritin

| Ferritin | 51 ng/ml | 30 - 400 | 51 |
|---|---|---|---|

Figure 9A

Patient Results Report

| PATIENT | DATE OF BIRTH | CKD STAGE | DATE OF SERVICE | PHYSICIAN |
|---|---|---|---|---|
| Patient 2, Sample | 04/15/1960 | 3 | 05/17/2006 | Physician, Sample |

Current Laboratory Results

| ANALYTE | RESULT UNIT | REFERENCE INTERVAL | LOW RESULT ( REF. INT. ) HIGH RESULT |
|---|---|---|---|
| Lipid Panel | | | |
| Total Cholesterol | 125 mg/dl | 100 - 199 | 125 |
| HDL | 67 mg/dl | >39 | 28 |
| Triglyceride | 66 mg/dl | 0 - 149 | 55 |
| LDL(calc) | 55 mg/dl | 0 - 99 | 55 |
| VLDL | 13 mg/dl | 0 - 30 | 13 |
| Non-HDL cholesterol | 58 mg/dl | 30 - 129 | 58 |

Figure 9B

LitholinkCKD

Patient Results Report — 1010

| PATIENT | DATE OF BIRTH | CKD STAGE | DATE OF SERVICE | PHYSICIAN |
|---|---|---|---|---|
| Patient 2, Sample | 04/15/1960 | 3 | 05/17/2006 | Physician, Sample |

KDOQI™ Based Analysis and Treatment Options eGFR, Blood Pressure, and Proteinuria

1020 Estimated GFR (all values) is not changing significantly with time. Systolic Blood Pressure is above goal and has not changed significantly, was 135 and now is 140 mm Hg. Diastolic Blood Pressure is within goal and has decreased, was 82 and now is 80 mm Hg. Potassium is within goal and has decreased, was 5.2 and now is 4.3 mmol/l. Your office reports ACEI or ARB treatment is used and diuretic treatment is not being used. ADA recommends hemoglobin A1C should be obtained every 3 months in a diabetic.

| GENDER | DIABETES | SELF-REPORTED RACE | CURRENT eGFR | MOST RECENT CKD STAGE |
|---|---|---|---|---|
| M | Yes | White-Caucasian | 47 | 3 |

Treatment Suggestions [1]

Consider increase of ACEI or ARB (within the recommended range). Confirm adherence to antihypertensive therapy. Consider thiazide diuretic. Lifestyle should include sodium intake of 2300 to 3000 mg/d, exercise (30 minutes 5 times a week), less than three alcoholic drinks per day, a low dose (81 mg) aspirin daily, and smoking cessation.

Follow-Up Suggestions [1]

Hemoglobin A1C and Spot Urine Panel (Albumin preferred) are due; fasting Renal Panel within 1 month.

months (since enrollment)

KDOQI™ Flow Sheet

The table below shows the 8 most recent results as well as the treatments your office reported.

| Date | K | BUN | SCr | eGFR | HB A1c | Protein/Cr (mg/g) | Alb/Cr (ug/mg) | Weight (kg) | Systolic[3] | Diastolic | ACEI/ARB | Diuretic |
|---|---|---|---|---|---|---|---|---|---|---|---|---|
| 05/17/06 | 4.3 | 26 | 1.60 | 47 | | | | 72.1 | 140 | 80 | Yes | No |
| 02/27/06 | 5.2 | 34 | 1.50 | 51 | | | | 70.3 | 135 | 82 | Yes | No |
| 01/03/06 | 4.4 | 41 | 1.50 | 51 | | | | 74.4 | ? | ? | Yes | No |
| 01/13/05 | 4.8 | 25 | 1.70 | 44 | | 176 | | 74.4 | 135 | 78 | Yes | No |

Figure 10

LitholinkCKD

Patient Results Report

| PATIENT | DATE OF BIRTH | CKD STAGE | DATE OF SERVICE | PHYSICIAN |
|---|---|---|---|---|
| Patient 2, Sample | 04/15/1960 | 3 | 05/17/2006 | Physician, Sample |

Bone & Mineral

Intact PTH is above goal and has not changed significantly, was 82 and now is 89 pg/ml. Phosphorus is within goal and has risen, was 3.2 and now is 4.1 mg/dl. Corrected Calcium is within goal and has risen, was 8.7 and now is 9.1 mg/dl. Carbon Dioxide is within goal and has risen, was 17 and now is 25 mmol/l. Vitamin D deficiency is present (was 8 and now is 9 ng/ml). Your office reports low phosphate diet, phosphate binders, active vitamin D analog, vitamin D, and alkali treatments are not being used.

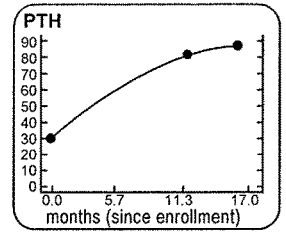

Treatment Suggestions [1]

Begin vitamin D (ergocalciferol 50,000 IU/week orally for 4 weeks then monthly for 5 months; alternatively, cholecalciferol 2000 IU/d for 6 months). Restrict diet phosphate to 800 - 1000 mg/d. Phosphate binder would be used to lower PTH, if 25-hydroxy vitamin D was in the normal range. Active vitamin D would be appropriate, if 25-hydroxy vitamin D was not presently below goal (30 ng/ml).

Follow-Up Suggestions [1]

Fasting Renal Panel within 1 month; fasting PTH with Renal Panel within 3 months; 25-Hydroxy Vitamin D within 6 months.

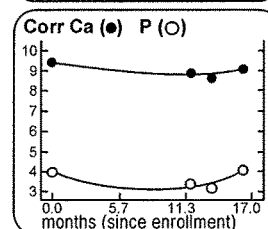

Lipids

LDL is within goal and has decreased, was 135 and now is 55 mg/dl. Triglyceride is within goal and has decreased, was 91 and now is 66 mg/dl. Non-HDL Cholesterol is within goal and has decreased, was 153 and now is 58 mg/dl. HDL is within goal and has not changed significantly, was 63 and now is 67 mg/dl. Your office reports statin treatment is used and fibrate and niacin treatments are not being used.

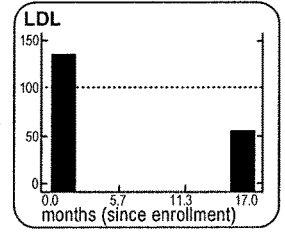

Treatment Suggestions [1]

Therapeutic lifestyle changes are always valuable to maintain optimal blood lipid status (diet, exercise, weight management). Continue statin. Lipid status is acceptable.

Follow-Up Suggestions [1]

Fasting Lipd Panel within 3 months.

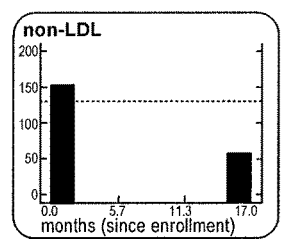

Anemia

Hemoglobin is low and has not changed significantly, was 12.2 and now is 12.2 g/dl. TSAT is within goal and has risen, was 13.0 and now is 21.0 %. Ferritin is below goal and has risen, was 23 and now is 51 ng/ml. Your office reports iron treatment is used and ESA treatment is not being used.

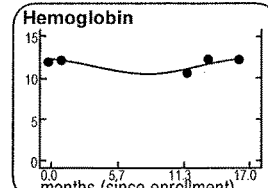

Treatment Suggestions [1]

Confirm adherence to iron therapy, taken away from meals. Increase oral or IV iron therapy.

Follow-Up Suggestions [1]

Fe/TIBC (TSAT) and Ferritin with CBC within 3 months.

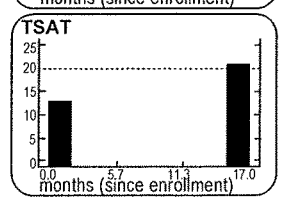

Figure 11

LitholinkCKD

Patient Results Report ⟵1210

| PATIENT | DATE OF BIRTH | CKD STAGE | DATE OF SERVICE | PHYSICIAN |
|---|---|---|---|---|
| Patient 2, Sample | 04/15/1960 | 3 | 05/17/2006 | Physician, Sample |

KDOQI™ Flow Sheet

The table below shows the 8 most recent results as well as the treatments your office reported.

Bone & Mineral

| DATE | PTH | P | Corr Ca | $CO_2$ | K | 25-D | LPD | PB | CaPB | AVD | VitD | ALKALI |
|---|---|---|---|---|---|---|---|---|---|---|---|---|
| 05/17/06 | 89 | 4.1 | 9.1 | 25 | 4.3 | 9.0 | No | No | No | No | No | No |
| 02/27/06 |    | 3.2 | 8.7 | 17 | 5.2 |    | No | No | No | No | No | No |
| 01/03/06 | 82 | 3.4 | 8.9 | 17 | 4.4 | 8.0 | No | No | No | No | No | No |
| 01/13/05 | 29 | 4.0 | 9.4 | 25 | 4.8 |    | No | No | No | No | No | No |

Lipids

| DATE | LDL | TG | NON-HDL | CHOL | MDL | STATIN | FIBRATE | NIACIN | FASTING |
|---|---|---|---|---|---|---|---|---|---|
| 05/17/06 | 55 | 66 | 58 | 125 | 67 | Yes | No | No | Yes |
| 02/10/05 | 135 | 91 | 153 | 216 | 63 | No | No | No | Yes |

Anemia

| TEST DATE | Hb | TSAT | FERRITIN | IRON | ESA |
|---|---|---|---|---|---|
| 05/17/06 | 12.2 | 21.0 | 51 | Yes | No |
| 02/27/06 | 12.2 |      |    | Yes | No |
| 01/03/06 | 10.8 |      |    | Yes | No |
| 02/10/05 | 12.1 | 13.0 | 23 | Yes | No |
| 01/13/05 | 12.1 |      |    | Yes | No |

Figure 12

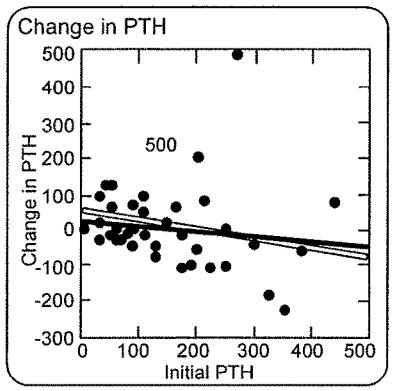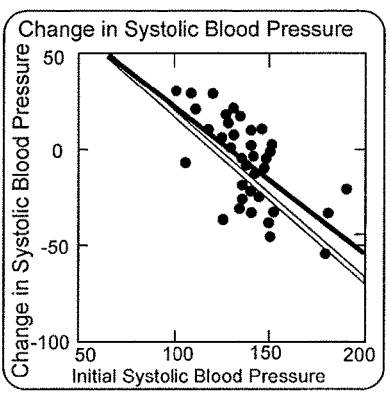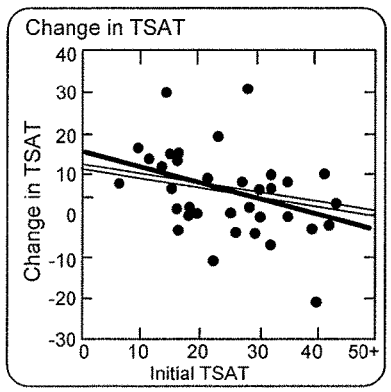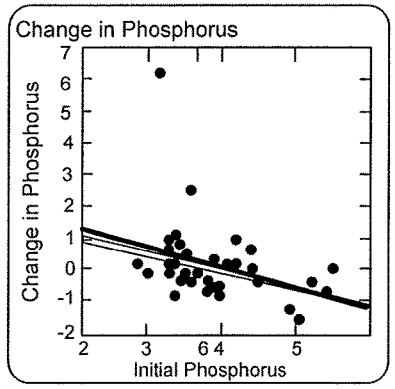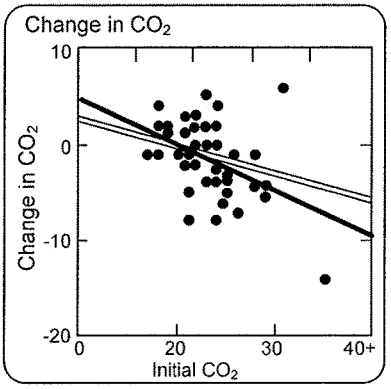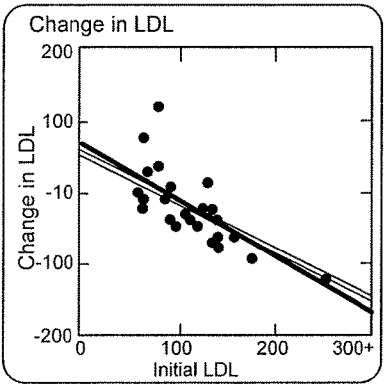
Figure 12B

LitholinkCKD

Quarterly Report

| PHYSICIAN | PRACTICE | REPORT TIMEFRAME |
|---|---|---|
| Sample, Patient | Sample Nephrology | 1st Quarter 2009 |

Patients Suggested for Follow-Up Testing

| PATIENT | DATE OF BIRTH | LAST TEST COMPLETED | PLEASE TEST THIS PATIENT |
|---|---|---|---|
| Patient, Patientname | 11/16/1953 | 06/02/2009 | ☐ Urine Panel  ☐ Blood  ☐ Other: |
| Patient, Patientname | 11/16/1953 | 06/02/2009 | ☐ Urine Panel  ☐ Other: |
| Patient, Patientname | 11/16/1953 | 06/02/2009 | ☐ Urine Panel  ☐ Other: |
| Patient, Patientname | 11/16/1953 | 06/02/2009 | ☐ Urine Panel  ☐ Blood  ☐ Other: |
| Patient, Patientname | 11/16/1953 | 06/02/2009 | ☐ Blood  ☐ Other: |
| Patient, Patientname | 11/16/1953 | 06/02/2009 | ☐ Urine Panel  ☐ Blood  ☐ Other: |
| Patient, Patientname | 11/16/1953 | 06/02/2009 | ☐ Urine Panel  ☐ Blood  ☐ Other: |
| Patient, Patientname | 11/16/1953 | 06/02/2009 | ☐ Urine Panel  ☐ Other: |
| Patient, Patientname | 11/16/1953 | 06/02/2009 | ☐ Urine Panel  ☐ Blood  ☐ Other: |
| Patient, Patientname | 11/16/1953 | 06/02/2009 | ☐ Blood  ☐ Other: |
| Patient, Patientname | 11/16/1953 | 06/02/2009 | ☐ Urine Panel  ☐ Blood  ☐ Other: |
| Patient, Patientname | 11/16/1953 | 06/02/2009 | ☐ Urine Panel  ☐ Blood  ☐ Other: |
| Patient, Patientname | 11/16/1953 | 06/02/2009 | ☐ Urine Panel  ☐ Other: |
| Patient, Patientname | 11/16/1953 | 06/02/2009 | ☐ Urine Panel  ☐ Blood  ☐ Other: |
| Patient, Patientname | 11/16/1953 | 06/02/2009 | ☐ Urine Panel  ☐ Blood  ☐ Other: |

Fax this form to Litholink at 312 243 3297.

| PHYSICIAN NAME | SIGNATURE | DATE |
|---|---|---|

☐ Please discontinue this service.

Figure 12C

Figure 14
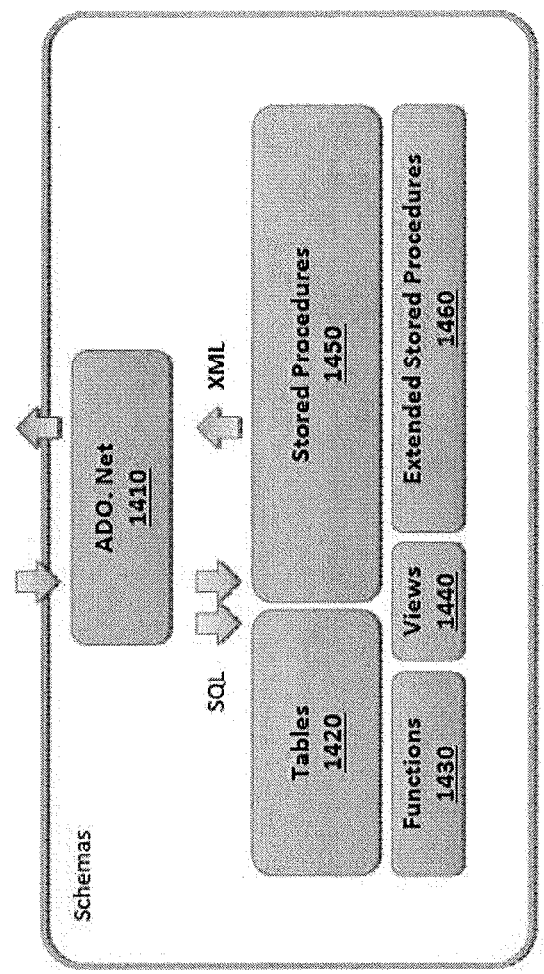
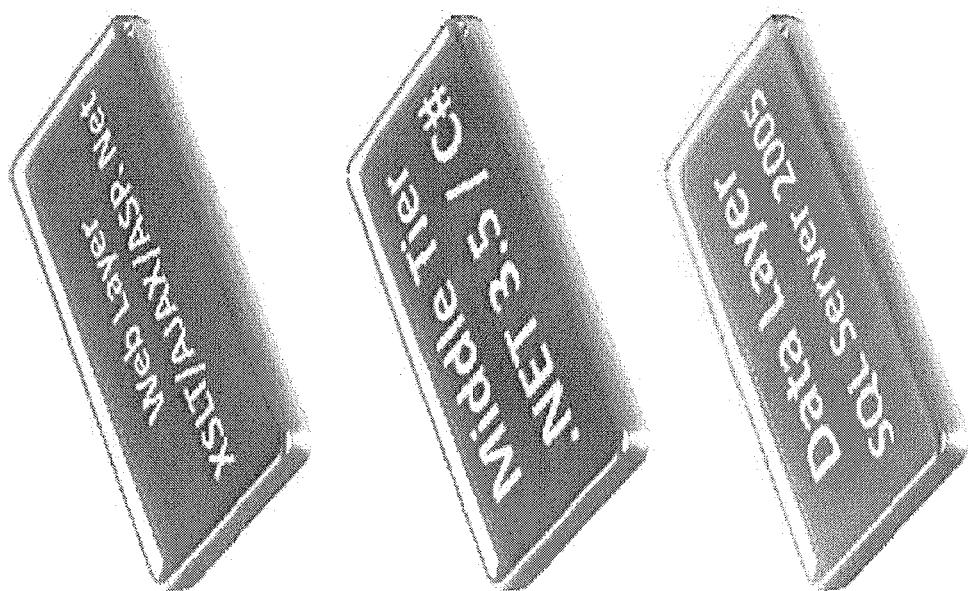

Patient Data Flow

| *LL*:Paragraphs | | | |
|---|---|---|---|
| = xmlns:*LL* | | http://www.litholink.com/dsl/ckd | |
| *LL*:ActiveDomainList | | | |
| | | = | DiseaseID | 2 |
| | | | ActiveDomain (4) | |
| *LL*:Domain | | | |
| | | = | Type | Anemia |
| | | {} | SampleType | Serum |
| | | | AssessmentList | |
| | | | Additions | |
| | | | FollowUp | |
| | | | SegmentList | |
| | | | SubMatrix (4) | |
| | | | Matrix (2) | |
| *LL:Domain* Type=BoneAndMineral | | | |
| *LL:Domain* Type=Lipds | | | |
| *LL:Domain* Type=eGFR | | | |

FIGURE 19

| *LL:*ActiveDomainList | | |
|---|---|---|
| | = DiseaseID | 2 |
| | ActiveDomain | eGFR |
| | ActiveDomain | BoneAndMineral |
| | ActiveDomain | Lipids |
| | ActiveDomain | Anemia |

| *LL:* Domain | | |
|---|---|---|
| | = Type | Lipds |
| | SampleType | Serum |
| | AssessmentList | |
| | Additions | |
| | FollowUp | |
| | SegmentList | |
| | Matrix Type=Lipids | |
| | SubMatrix Type=Lipids1 | |
| | SubMatrix Type=Lipids2 | |

FIGURE 20

| AssessmentList | | | | |
|---|---|---|---|---|
| | Assessment (3) | | | |
| | | | Abc Text | |
| | | 1 | Hb | |
| | | 2 | TSAT | |
| | | 3 | Ferritin | |
| | ReportedValue (2) | | | |
| | | | = Name | Abc *Text* |
| | | 1 | ESA | ESA |
| | | 2 | iron | Iron |

FIGURE 21

| Additions | | |
|---|---|---|
| Sentence Type=Assessment Position=End | | |
| Sentence Type=Assessment Position=End | | |
| Sentence Type=Assessment Position=End | | |
| Sentence Type=Assessment Position=End | | |
| Sentence Type=Assessment Position=End Tag=ESA15 | | |
| Sentence Type=Assessment Position=Beginning | | |
| Sentence | | |
| | = Type | Treatment |
| | = Position | End |
| | = Tag | Fe4 |
| | Condition | ESA no and Iron no and Ferritin greater than 500 and TSAT greater than 50 |
| | Text | Consider evaluation for hemochromatosis or iron overload. |

FIGURE 22

| | FollowUp | | | |
|---|---|---|---|---|
| | Time (14) | | | |
| | | = Tag | ◊ Desc | ◊ Weeks |
| | 1 | T0 | Due now | 1 |
| | 2 | T02 | 2 weeks | 2 |
| | 3 | T1 | 1 month | 4 |
| | 4 | T2 | 2 months | 9 |
| | 5 | T3 | 3 months | 13 |
| | 6 | T4 | 4 months | 17 |
| | 7 | T5 | 5 months | 21 |
| | 8 | T6 | 6 months | 26 |
| | 9 | T7 | 7 months | 30 |
| | 10 | T8 | 8 months | 34 |
| | 11 | T9 | 9 months | 39 |
| | 12 | T10 | 10 months | 43 |
| | 13 | T11 | 11 months | 47 |
| | 14 | T12 | 12 months | 52 |
| | Measurement (3) | | | |
| | | = Tag | = KDOQI | ◊ PrimaryChemistry | ◊ Desc |
| | 1 | M5 | 1 | Hb | CBC |
| | 2 | M6 | 1 | Ferritin | Ferritin |
| | 3 | M7 | 1 | TSAT | Fe/TIBC (TSAT) |

FIGURE 23

| SegmentList | |
|---|---|
| | Segment (51) |

| Segment | | |
|---|---|---|
| | = Tag | Fe1 |
| | = KDOQI | 1 |
| | ◊ Measurement | M5-T3, M6-T3, M7-T3 |
| | ◊ Text | Continue Iron therapy. |

FIGURE 24

| ▲ Matrix | | | | | |
|---|---|---|---|---|---|
| = Type | Potassium | | | | |
| ▼ Structure | | | | | |
| ▲ Condition (6) | | | | | |
| | | = Co2 | = K | {} Alkali_yes | {} Alkali_no | {} Alkali_unknown |
| | 1 | H | H | K2, K5 | K5 | K2, K5 |
| | 2 | N | H | K5 | K5 | K5 |
| | 3 | L | H | K4, K5 | K4, K5 | K4, K5 |
| | 4 | H | L | K1 | K1 | K1 |
| | 5 | N | L | - | - | - |
| | 6 | L | L | K3 | K3 | K3 |

| ▲ SubMatrix | | | | | |
|---|---|---|---|---|---|
| = Type | Diuretic | | | | |
| ▲ Structure | | | | | |
| | ▲ InterrogatorList | | | | |
| | | = EvaluationType | and | | |
| | | ▲ Interrogator (2) | | | |
| | | | | = type | = condition | Abc Text |
| | | | 1 | SelectStatus | | Diuretic |
| | | | 2 | Evaluation | [Chemistry!eGFR!T3] less than 50 | eGFR_evaluate |
| ▲ Condition (4) | | | | | |
| | | = Diuretic | = eGFR_evaluate | {} Alkali_yes_H | {} Alkali_no_H |
| | 1 | Yes | Yes | D1 | D1, D6 |
| | 2 | Yes | No | (SBP greater than 150 ? D4: D2) | (SBP greater than 150 ? D5, D6:D6) |
| | 3 | No | Yes | D3 | (SBP greater than 150 ? D3, D6:D6) |
| | 4 | No | No | D5 | (SBP greater than 150 ? D3, D6:D6) |

FIGURE 26

CLINICAL LABORATORY-BASED DISEASE MANAGEMENT PROGRAM, WITH AUTOMATED PATIENT-SPECIFIC TREATMENT ADVICE

CROSS-REFERENCE TO RELATED APPLICATION

This application is a continuation of U.S. patent application Ser. No. 17/516,928, filed Nov. 2, 2021, which is a continuation of U.S. patent application Ser. No. 16/403,915, filed May 6, 2019, now patented as U.S. Pat. No. 11,195,603, issued on Dec. 7, 2021, which is a continuation of U.S. application Ser. No. 13/755,361, filed Jan. 31, 2013, now patented as U.S. Pat. No. 10,290,369, issued on May 14, 2019, which is a continuation of U.S. patent application Ser. No. 12/535,287, filed Aug. 4, 2009, now abandoned, which claims the benefit of U.S. Provisional Application No. 61/086,023, filed Aug. 4, 2008, the entirety of each of which is hereby incorporated by reference.

FIELD OF THE PRESENT INVENTION

The present invention relates to systems and methods for providing a clinical laboratory-based disease management program with automated patient-specific treatment advice.

BACKGROUND

Treatment of diseases can be challenging. This is especially true when the disease is complex. In these cases, medical service providers such as doctors have a limited window of time in which to make critical decisions regarding patient treatment and care. When dealing with a complex medical condition, the medical provider may be faced with a voluminous amount of information from which to determine the proper course of treatment. Yet the patient's situation may be such that the medical provider does not know or does not have the time to adequately review all of the relevant information regarding the proper standard of care.

An example of such a complex case is Chronic Kidney Disease (CKD). CKD is the material loss of function of the kidneys and it involves a combination of several other common, complex diseases. CKD is primarily caused by diabetes and high blood pressure but it also causes or complicates high blood pressure, cardiovascular disease, bone and mineral diseases and anemia, among other conditions. CKD is currently a public health crisis affecting an estimated 26 million Americans and doing irreparable damage to vital body functions, yet most people with CKD are unaware they have the condition.

Other examples of poorly treated complex diseases include osteoporosis and thyroid disease. Osteoporosis is a metabolic disturbance of the skeleton characterized by low bone mass and structural deterioration of bone, leading to bone fragility and an increased susceptibility to fracture, especially of the hip, spine, and wrist. Proper treatment of osteoporosis requires access to sophisticated bone density scanning technology, blood testing to rule out secondary causes of the disease which, if present, require different treatment, evidence based interpretations of the bone density and blood tests, understanding of treatment alternatives and their efficacy.

Thyroid disease occurs when the thyroid gland does not supply the proper amount of hormones needed by the body. If the thyroid is overactive, it releases too much thyroid hormone into the bloodstream, resulting in hyperthyroidism. An underactive thyroid produces too little thyroid hormone, resulting in hypothyroidism. Treating thyroid disease with maximum effectiveness requires testing of different dosages of complex medications with often frustrating imbalances over time for the patient and the physician.

It is widely recognized that the complexity of treatment of diseases such as CKD and others as well as the growth of new treatments and of medical research into the effectiveness of existing treatments makes it a daunting task for physicians to know and practice at the state of the art. Embodiments of the present invention address this problem by, for example, making the clinical laboratory the organizer, integrator and interpreter of the primary data that is necessary for a physician to understand, treat and prevent chronic kidney disease.

SUMMARY

Embodiments of the present invention provide methods and systems that may improve the quality of care provided to an individual by integrating data relating to the individual and a proposed action to assist a caregiver providing care to the individual. Some embodiments include generating a proposed action, or proposed actions, for the caregiver in view of the integration of data relating to the individual. A program for the individual may comprise one or more proposed actions.

Embodiments of the present invention may be advantageously utilized in numerous environments including, but not limited to: healthcare, including primary healthcare, disease management, rehabilitation, physical therapy and the like; diet and nutrition; training and exercise; and similar environments where the quality of an action undertaken by an individual may be improved by the integration of a plurality of data points relating to the individual. Features and advantages of the present invention are described herein with reference to the healthcare environment wherein data relating to the individual may comprise diagnostic test data, for example data generated by a clinical testing laboratory, and may further comprise additional data relating to the individual that may not be generated from a test or analysis, for example ethnicity data, geographic data, economic data, prior treatment data, and the like. One or more data points from the diagnostic testing and/or additional data may be integrated with a proposed action for the individual.

In a healthcare environment, an embodiment of the present invention may integrate data relating to an individual with standard-of-care guidelines for a particular condition affecting the individual and/or a desired outcome for the individual. In an embodiment, data relating to the individual is compared to standard-of-care guidelines to generate a proposed action for the individual. Standard-of-care guidelines in the healthcare environment may comprise science-based guidelines generated by medical professionals and academics based on research and study of patient treatment programs and clinical outcomes. Standard-of-care guidelines for particular conditions or disease states may be promulgated by associations, foundations and or boards of healthcare professionals with experience relating to the disease state. Examples include, but are not limited to the National Kidney Foundation (the KDOQI™ guidelines), the American Diabetes Association, the American Cancer Society, Kidney Disease: Improving Global Outcomes (KDIGO®), and similar organizations. The U.S. Government, through the Health and Human Services Department has established a National Guideline Clearinghouse to provide healthcare professionals with access to information relating to standard-of-care guidelines.

In general, standard-of-care guidelines recommend an action, or actions, to be undertaken by an individual having a particular condition or disease state. An action may comprise taking of a pharmaceutical composition, modification of diet, modification of activity level and/or similar actions. As described herein, an embodiment of the present invention may advantageously generate an action for an individual in view of data relating to the individual and a standard of care guideline.

Additional description of the present invention is provided below with reference to embodiments in a healthcare environment and a particular disease state to promote understanding of the features and advantageous of the present invention. As will be apparent from the following description, the present invention is not limited to the specific embodiments herein described.

In one embodiment of the invention, a treatment management program (the "Litholink program") is provided in which a laboratory, for example a medical diagnostic testing laboratory performs testing, for example standard-of-care clinical testing, relating to the detection, treatment or monitoring of a medical condition and seamlessly integrates with the testing a variety of disease management services that assist a patient and physician in achieving the best possible patient outcome based on the test results and other relevant information. Further embodiments of the invention may comprise one or more disease management services.

One embodiment may comprise a software system by which state of the art, patient-specific treatment recommendations are provided to physicians on the test results report based on state of the art treatment guidelines for the medical condition adjusted according to the individual patient's lab results, treatment history and demographics.

In one embodiment, a method is provided, the method including receiving a test result data, wherein said test result data represents a result of a test on a physical specimen, associating said test result data with a standard-of-care data, wherein said standard-of-care data represents a recommended course of action for the condition represented by the test result data, and transforming said specimen data and said standard-of-care data into a human-readable form.

In another embodiment, a system is provided, the system including a processor, a software adapted to be executed on said processor, said software comprising instructions for receiving a test result data, wherein said test result data represents a result of a test on a physical specimen, associating said test result data with a standard-of-care data, wherein said standard-of-care data represents a recommended course of action for the condition represented by the test result data, and transforming said specimen data and said standard-of-care data into a human-readable form.

In a further embodiment, a method for providing a Disease-Specific Patient Report is provided, the method including receiving a test result data, wherein said test result data represents a result of a test on a physical specimen, performing a quality control step on the test result data, processing the test result data in order to identify whether the data fits into an acceptable range, or if the data is above or below the acceptable range, associating said test result data with a standard-of-care data, wherein said standard-of-care data represents a recommended course of action for the condition represented by the test result data, and transforming said specimen data and said standard-of-care data into a human-readable form, and providing said test result data and said standard-of-care data.

In one embodiment of the invention, a treatment management program (the "Litholink program") is provided in which a medical diagnostic testing laboratory performs standard-of-care clinical testing necessary to detect, treat and monitor a medical condition, as ordered by the patient's physician, and seamlessly integrates with the testing a variety of disease management services that assist the patient and physician in achieving the best possible patient outcome based on the test results and other relevant information. Examples of types of testing include blood testing, urine testing, EKG testing, stress testing, x-ray, colonoscopy, biopsy, and others. Further embodiments of the invention may comprise one or more disease management services.

One embodiment may comprise a software system by which state of the art, patient-specific treatment recommendations are provided to physicians on the test results report based on state of the art treatment guidelines for the medical condition adjusted according to the individual patient's lab results, treatment history and demographics.

In one embodiment, a method is provided, the method including receiving a test result data, wherein said test result data represents a result of a test on a physical specimen, associating said test result data with a standard-of-care data, wherein said standard-of-care data represents a recommended course of action for the condition represented by the test result data, and transforming said specimen data and said standard-of-care data into a human-readable form.

In another embodiment, a system is provided, the system including a processor, a software adapted to be executed on said processor, said software comprising instructions for receiving a test result data, wherein said test result data represents a result of a test on a physical specimen, associating said test result data with a standard-of-care data, wherein said standard-of-care data represents a recommended course of action for the condition represented by the test result data, and transforming said specimen data and said standard-of-care data into a human-readable form.

In a further embodiment, a method for providing a Disease-Specific Patient Report is provided, the method including receiving a test result data, wherein said test result data represents a result of a test on a physical specimen, performing a quality control step on the test result data, processing the test result data in order to identify whether the data fits into an acceptable range, or if the data is above or below the acceptable range, associating said test result data with a standard-of-care data, wherein said standard-of-care data represents a recommended course of action for the condition represented by the test result data, and transforming said specimen data and said standard-of-care data into a human-readable form, and providing said test result data and said standard-of-care data.

BRIEF DESCRIPTION OF THE FIGURES

FIGS. 1A and 1B are test order forms according to one embodiment;

FIG. 3 is the Medical Director's Notes section of a Patient Results Report according to one embodiment;

FIG. 5 is the portion of a Patient Results Report displaying summary eGFR, blood pressure, and proteinuria according to one embodiment;

FIG. 6 is a summary of co-morbidity status in a Patient Results Report according to one embodiment;

FIG. 7 is the Test Results and Treatments section of a Patient Results Report according to one embodiment;

FIGS. 9A and 9B is the Laboratory Results section of a Patient Results Report according to a further embodiment;

FIG. 10 is the portion of a Patient Results Report displaying summary eGFR, blood pressure, and proteinuria according to a further embodiment;

FIG. 11 is a summary of co-morbidity status in a Patient Results Report according to a further embodiment;

FIG. 12 is the Test Results and Treatments section of a Patient Results Report according to a further embodiment;

FIGS. 12A, 12B, and 12C depict an outcome according to one embodiment;

FIG. 14 depicts an ADO.NET software architecture that can be used to provide the application with access to the data stored in a database, according to one embodiment;

FIGS. 19-26 depict various protocols, domains, assessments, and lists according to one or more embodiments.

DETAILED DESCRIPTION

Figure 2:
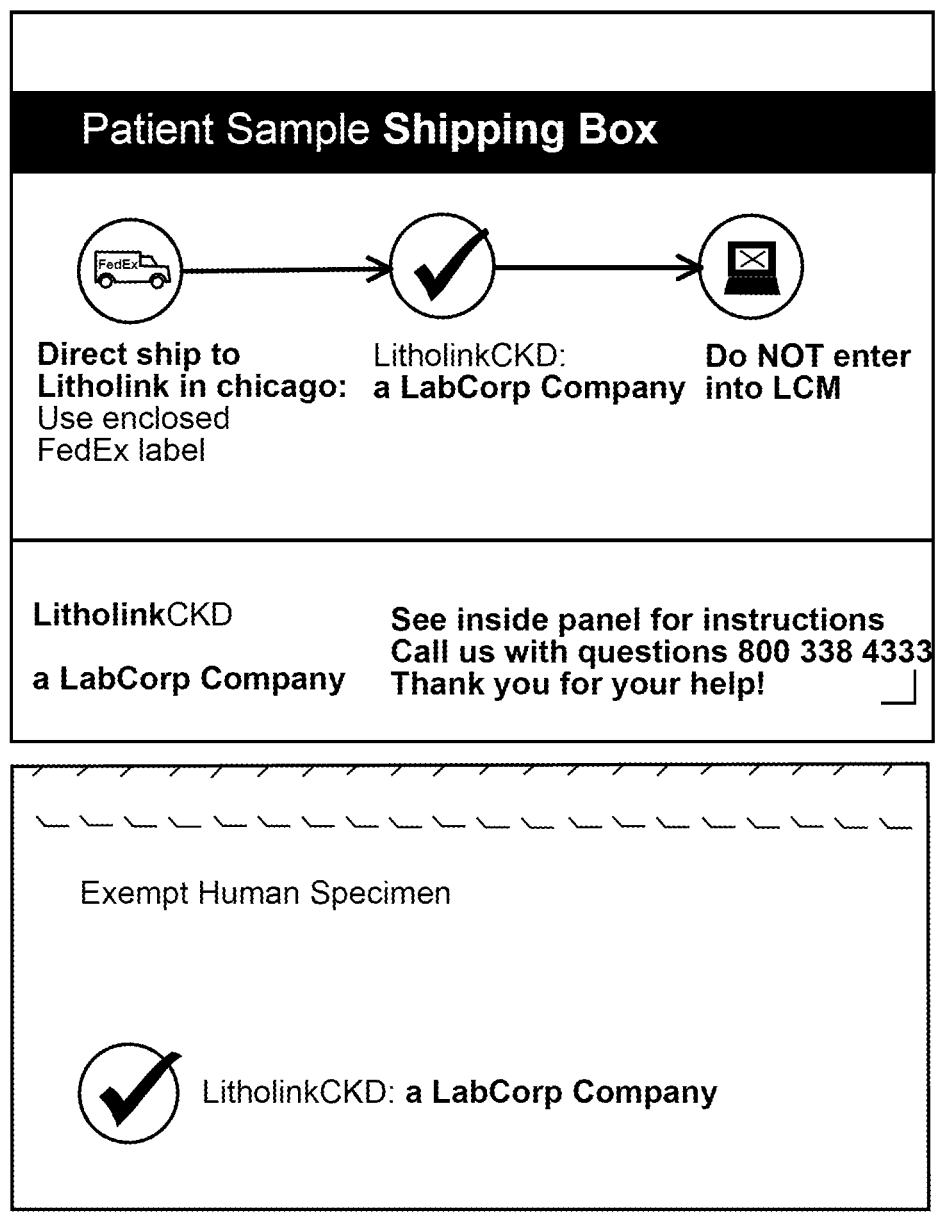
FIG. 2 is a patient sample shipping box according to one embodiment.

A Laboratory-Based Disease Management Program According to One Embodiment

In the context of treating a complex medical condition such as CKD, it is challenging for a medical provider, such as a doctor, to process the relevant information in order to provide treatment at the standard of care. There is no shortage of information regarding the treatment of such diseases and conditions, but this huge volume of information can add its own challenges. For example, the standard-of-care guidelines for CKD would comprise a set of multiple volumes. It is not reasonable to expect a doctor to read this voluminous information and apply it at the point of care in a usable way.

In order to assist doctors in providing proper care, there is a need for a way to direct doctors to the proper information that is relevant to the treatment of the patient's condition. Embodiments of the invention assist in meeting this and other needs. For example, in some embodiments, a computer assists the doctor at the point of care. The laboratory has access to lab data containing critical patient information resulting from tests, measurements, and procedures. Thus, it would be beneficial to provide a system and method that cross-references the lab data with standard-of-care information.

Because of the tremendous amount of information available to a doctor, it is important to provide patient care information in a form and manner that the doctor will read. One document that the doctor typically reads is the laboratory report. Thus, by providing information in the context of a laboratory report or as part of a laboratory report, this dramatically increases the likelihood that the doctor will read the information. One embodiment of the invention provides systems and methods for generating a laboratory report that includes information such as standard-of-care information based on the lab data.

One embodiment provides a method comprising receiving a test result data, wherein said test result data represents a result of a test on a physical specimen; associating said test result data with a standard-of-care data, wherein said standard-of-care data represents a recommended course of action for the condition represented by the test result data; and transforming said specimen data and said standard-of-care data into a human-readable form.

A further embodiment comprises providing said test result data and said standard-of-care data in the form of a laboratory report.

In one embodiment, the step of associating said test result data with a standard-of-care data comprises evaluating whether the test result data are below, within, or above a set of guidelines.

In a further embodiment, the set of guidelines comprises at least one of: KDOQI™, any other medical practices guidelines referenced by KDOQI™, JNC7, ATP III, Kidney Disease: Improving Global Outcomes (KDIGO®), or other medical practice guidelines which reflect a standard of care for complex diseases.

In one embodiment, the step of associating said test result data with a standard-of-care data comprises evaluating whether medication is being used.

One embodiment further comprises evaluating whether the test result data has changed from prior test results.

A further embodiment comprises providing information in human-readable form regarding any change in the test result data from prior test results.

In one embodiment, the step of associating said test result data with a standard-of-care data comprises using a matrix to query the relevant standard-of-care data for the test result data.

A further embodiment comprises determining whether an override condition exists, and transforming data representing the override condition into a human-readable form.

A further embodiment comprises associating at least one of demographic data, medication data, or prior test results with the standard-of-care data.

One embodiment provides a system comprising a processor, a software adapted to be executed on said processor, said software comprising instructions for receiving a test result data, wherein said test result data represents a result of a test on a physical specimen, associating said test result data with a standard-of-care data, wherein said standard-of-care data represents a recommended course of action for the condition represented by the test result data, and transforming said specimen data and said standard-of-care data into a human-readable form.

In one embodiment, the software further comprises instructions for providing said test result data and said standard-of-care data in the form of a laboratory report.

In a further embodiment, the instructions for associating said test result data with a standard-of-care data comprise instructions for evaluating whether the test result data are below, within, or above a set of guidelines.

In a further embodiment, the set of guidelines comprises either KDOQI™, any other medical practices guidelines referenced by KDOQI™, JNC7, ATP III, Kidney Disease: Improving Global Outcomes (KDIGO®), or other medical practice guidelines which reflect a standard of care for complex diseases.

In one embodiment, the step of associating said test result data with a standard-of-care data comprises evaluating whether medication is being used.

One embodiment further comprises evaluating whether the test result data has changed from prior test results.

A further embodiment comprises providing information in human-readable form regarding any change in the test result data from prior test results.

In one embodiment, the step of associating said test result data with a standard-of-care data comprises using a matrix to query the relevant standard-of-care data for the test result data.

A further embodiment comprises determining whether an override condition exists, and transforming data representing the override condition into a human-readable form.

A further embodiment comprises associating at least one of demographic data, medication data, or prior test results with the standard-of-care data.

On embodiment comprises a method for providing a Disease-Specific Report comprising receiving a test result data, wherein said test result data represents a result of a test on a physical specimen; performing a quality control step on the test result data; processing the test result data in order to identify whether the data fits into an acceptable range, or if the data is above or below the acceptable range; associating said test result data with a standard-of-care data, wherein said standard-of-care data represents a recommended course of action for the condition represented by the test result data; transforming said specimen data and said standard-of-care data into a human-readable form; and providing said test result data and said standard-of-care data.

In a further embodiment, the standard-of-care data relates to Chronic Kidney Disease.

One embodiment of the invention includes a new way to use the clinical laboratory for the treatment of chronic kidney disease. In one embodiment, the programmatic model consists of ten distinct yet integrated functions, only one of which is routinely provided by clinical laboratories today yet all of which are important to properly treat a complex chronic disease like kidney disease. The elements are:

Thought leaders elucidate standard of care
Physician and patient education
Ordering guidance
High quality testing and service
Sophisticated clinical guidance
Outcomes feedback
Expert consultation
Compliance programs
Research In some embodiments, the Litholink program may comprise one or more of the following steps.

A. Ordering the Test and Gathering Patient Information

In one embodiment, the Litholink program is available to a physician after the patient has been diagnosed with CKD or other condition. Using CKD as an example, but not limiting the application to CKD, a CKD test order form may be provided by Litholink to physicians. FIGS. 1A and 1B are test order forms according to one embodiment. The test form may ask the physician to identify a specific diagnosis, the tests of blood and urine needed for detection and treatment, the patient's existing medications and the patient's demographics (e.g., sex, age, ethnicity). On the bottom of the test form is a space for the phlebotomist who does the blood draw to report the collection times and fasting information. The tests performed at the lab may include one or more of: a standard renal panel to detect and measure CKD's progression, a standard lipid panel to detect and treat related cardiovascular disease, the common tests for anemia and tests to detect and measure bone and mineral disorders associated with CKD. The back of the test form may include descriptions of some or all of the tests in the panels.

In some embodiments, the patient may provide the sample to the lab via mail, courier, or other shipping service such as UPS or FedEx. FIG. 2 is a patient sample shipping box according to one embodiment. In various embodiments, such a shipping box may include instructions regarding handling and processing the sample.

In some embodiments, after a physician has selected a patient for the program, ordered testing using the CKD test Request Form, and provided the other patient information requested, the order form is given to the patient who takes it to a service provider location, such as a Laboratory Corporation of America Holdings (LabCorp) Patient Service Center (PSC). In additional embodiments, the order form is faxed by a physician to a service provider such as Litholink. The patient may be given a copy of the form. The patient may then be registered. In one embodiment, the patient is registered in Litholink's proprietary software system called SOAR.

B. CKD Sample Processing

At the PSC, a phlebotomist may read the physician order and collect the appropriate patient samples in the appropriate tube. The phlebotomist may fill out draw dates and times on the Test Request Form, may place the form along with sample specimens into packaging for shipment to a LabCorp testing facility.

In some embodiments, the results are then sent electronically to Litholink where the patient may be registered and the test results uploaded in Litholink's proprietary software system called SOAR. In one embodiment, the patient is registered in Litholink's proprietary software system called SOAR. In one embodiment, SOAR is an N-Tier, open architecture, component-based software system using C#, Microsoft SQL Server 2005 and XML technology. In various embodiments, other architectures may be used, such as those based on WebSphere, Java, and other platforms known in the art.

Within a 24 hour turnaround time, the CKD Patient Results Report may be generated in SOAR.

C. CKD Patient Results Report

In some embodiments, the CKD Patient Results Report consists of 5 sections. Additional embodiments may include a subset of these sections. Further embodiments may include additional sections. These sections are depicted in two embodiments—FIGS. 3-7 and 8-12:

Section 1—Medical Director's Notes. This section is depicted in FIG. 3 according to one embodiment and FIG. 8 according to another embodiment.

Figure 4:
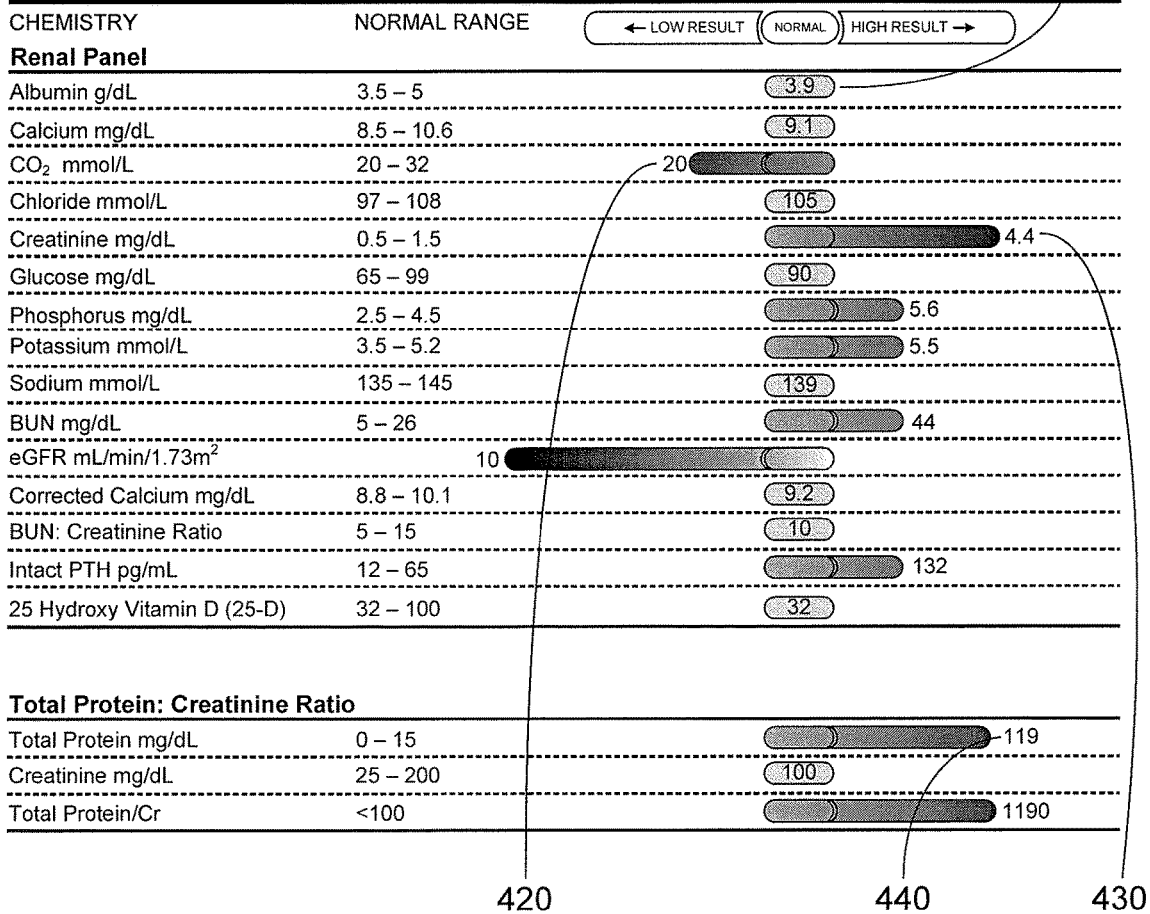
FIG. 4 is the Laboratory Results section of a Patient Results Report according to one embodiment.

Section 2—Laboratory Results. This section is depicted in FIG. 4 according to one embodiment and FIGS. 9A and 9B according to another embodiment.

Section 3—Summary eGFR, blood pressure, and proteinuria with treatment and follow-up options. This section is depicted in FIG. 5 according to one embodiment and FIG. 10 according to another embodiment.

Section 4—Summary of co-morbidity status. This section is depicted in FIG. 6 according to one embodiment and FIG. 11 according to another embodiment.

Section 5—Test Results and Treatments for co-morbidities. This section is depicted in FIG. 7 according to one embodiment and FIG. 12 according to another embodiment.

1. Section 1—Medical Director's Notes

FIG. 3 is the Medical Director's Notes section of a Patient Results Report according to one embodiment. In some embodiments, a Patient Results Report may include a section with some information regarding the patient (e.g., name and date of birth), the patient's physician, and any notes from a medical director. In some embodiments, this is the first page of a Patient Results Report.

Figure 8:
FIG. 8 is the Laboratory Director's Notes section of a Patient Results Report according to a further embodiment.

FIG. 8 is the Laboratory Director's Notes section of a Patient Results Report according to a further embodiment. In some embodiments, a Patient Results Report may include a section with some information regarding the patient (e.g., name, date of birth, disease stage, and date of service), the patient's physician, and any notes from a laboratory director. In some embodiments, this is the first page of a Patient Results Report.

2. Section 2—Laboratory Results

In some embodiments, Section 2 (FIGS. 4, 9A, and 9B) may present the values of some or all tested chemistries and where they fall within the normal range. FIG. 4 is the Laboratory Results section of a Patient Results Report according to one embodiment. In the example depicted in FIG. 4, the Patient Results Report depicts results from a renal panel. For results that are within a normal range, the result is depicted under the heading "Normal." An example of this is the Albumin value 410.

In one embodiment, when a value is below the normal range, the value is displayed to the left of where a "Normal" value would be displayed. For example, see the $CO_2$ value 420. In a further embodiment, a below-normal value is positioned further left the further below normal it is. Thus, in such embodiments if the value is only slightly below the normal range, it will be positioned only slightly left of center. But if the value is further below normal, it will be positioned further left of center.

In one embodiment, when a value is above the normal range, the value is displayed to the right of where a "Normal" value would be displayed. For example, see the Creatinine value 430. In a further embodiment, an above-normal value is positioned further right the further above normal it is. Thus, in such embodiments if the value is only slightly above the normal range, it will be positioned only slightly right of center. But if the value is further above normal, it will be positioned further right of center.

In a further embodiment, when a value is significantly above or below the normal range, an attention-grabbing shading is presented beside the numerical value. Such a shading may be dark, bright, red, black, or any color scheme that may serve to attract the attention of the reader. A benefit of such a feature is that it may alert the reader (such as a doctor or other medical provider) that the value is far outside the normal range. An example can be found in the Total Protein value 440.

FIGS. 9A and 9B is the Laboratory Results section of a Patient Results Report according to a further embodiment. In addition to the features described above in connection with FIG. 4, the Patient Results Report depicted in FIGS. 9A and 9B contains additional features. For example, the Report provides information regarding the patient's stage of CKD and the date of service 910. Further, the Report provides additional data regarding the blood sample from which the results were obtained, such as blood draw date, draw time, and whether the patient was fasting 920. Such additional data may be relevant to evaluating and providing treatment to the patient; thus providing such data to the reader of the Report can be beneficial. As will be understood by others skilled in the art, removing and/or adding other data to/from the report is within the scope of the invention.

3. Section 3—Summary eGFR with Treatment and Follow-Up Options

FIG. 5 is the portion of a Patient Results Report displaying summary eGFR, blood pressure, and proteinuria according to one embodiment. The summary eGFR, blood pressure, and proteinuria depicted in FIGS. 5 and 10 may graphically present one or more eGFR test results over time, (e.g., from the oldest recorded test to the most recent test). The Summary eGFR may present the eGFR test results in a format that also shows the stage of CKD disease for the patient over time. In one embodiment, the 10 most recent tests are highlighted in brackets. The interval of time to progression to CKD stage 5 is estimated.

In addition, treatment and follow-up treatment options regarding the progression of CKD, including medication dosage information, based on eGFR and blood pressure data, relevant medications and demographic data, may be presented. For example, they may be presented in short narrative sentences of treatment advice, as depicted in FIG. 5. All reported treatment options are specific to the particular characteristics of the individual patient. The options for treatment may be based on a highly regarded set of guidelines for CKD care, such as the KDOQI™ guidelines established through the National Kidney Foundation and are discussed in more detail herein. In some embodiments, at the bottom of the eGFR test results, spot urine albumin tests for proteinuria, and blood pressure data are recorded sequentially. Other guidelines include the Seventh Report of the Joint National Committee on Prevention, Detection, Evaluation, and Treatment of High Blood Pressure (JNC7) promulgated by the National Heart Lung and Blood Institute of the National Institutes of Health.

In some embodiments, an explanation of the report is provided 510. This may be beneficial, for example, by assisting the reader (e.g., doctor or other medical provider) in using the data provided. Thus, the reader may be able to better utilize the data in providing treatment to the patient.

In some instances, the patient has a history of test results. In such cases, the Summary eGFR Report may also include a summary of one or more trends identified from the history of test results 520. Such a summary may also include one or more caveats, such as limitations resulting from information that is not available.

In some embodiments, a report may include treatment options 530. The treatment options may be the result of analyzing the test results in the context of a set of standard-of-care information and/or other relevant data.

In some embodiments, a report may include follow-up options 540. The follow-up options may be the result of analyzing the test results in the context of a set of standard-of-care information and/or other relevant data.

In some embodiments, a report includes one or more sets of test results 550. In cases where the patient has had multiple instances of a particular test, the report may show the results from these instances. In the report depicted in FIG. 5, ten eGFR tests are shown, with the most recent at the top, and descending chronologically. Benefits to displaying multiple test results include the ability to show trends and better understand the progression of the patient's condition.

In some embodiments, a report may include a graphical representation of the test results 560. The data points on the graphical representation may include data from previous tests. Benefits include the ability to show trends and better understand the progression of the patient's condition.

FIG. 10 is the portion of a Patient Results Report displaying summary eGFR, blood pressure, and proteinuria according to a further embodiment. The report depicted in FIG. 10 is based on KDOQI™ data. Various embodiments may utilize KDOQI™ or any other set of information that is beneficial. In one embodiment, the report includes information identifying the patient's stage of CKD 1010. Further embodiments may contain other information that is helpful to the reader.

In the embodiment depicted in FIG. 10, the report is based on testing the eGFR, Blood Pressure, and Proteinuria. Such data may be used in generating the summary 1020.

4. Section 4—Summary of Co-Morbidity Status

FIG. 6 is a summary of co-morbidity status in a Patient Results Report according to one embodiment. In some embodiments, section 4 of the test results report (FIGS. 6 and 11) provides a "thumbnail" graph of the test results over time for several of the most complex co-morbidities of CKD—e.g., bone and mineral disease, lipidemia, and anemia. Section 4 may also provide options for treatment, again based on the information provided by the physician on the Test Request Form, chemistry results, and the KDOQI™ and other authoritative guidelines or expert judgment.

In one embodiment, as depicted in FIG. 6, the report includes a summary of the of historical test data 610. This summary may be generated by methods and systems disclosed herein. For example, the summary may be generated based on historical test data as well as other sources of information, such as medical records.

In one embodiment, the report includes a description of the of treatment options 620. This description may be generated by methods and systems disclosed herein. For example, the description may be generated based on current and historical test data as well as other sources of information, such as medical records.

In one embodiment, the report identifies one or more follow-up options 630. These options may be generated by methods and systems disclosed herein. For example, they may be generated based on historical test data as well as other sources of information, such as medical records and/or standard-of-care data such as KDOQI™ guidelines.

In one embodiment, the report includes one or more graphs, which may depict information such as trends of historical test data 640. These graphs may be generated by methods and systems disclosed herein. For example, the graphs may be generated based on historical test data as well as other sources of information.

FIG. 11 is a summary of co-morbidity status in a Patient Results Report according to a further embodiment. Embodiments may include additional information, such as the patient's stage of CKD, data of service and/or other information 1110.

5. Section 5—Test Results and Treatments for Co-Morbidities

FIG. 7 is the Test Results and Treatments section of a Patient Results Report according to one embodiment. In some embodiments, section 5 of the Patient Results Report lists test results (FIGS. 7 and 12) next to the related treatments prescribed by the physician. This section may allow the physician to view the results as he/she changes treatments and thus see how his/her patients are responding to therapy over time.

For example, FIG. 7 depicts a report listing historical test results. For example, such a report may be broken down into sub-parts, such as "Bone & Mineral," "Lipids," and "Anemia." In some embodiments, a report may include historical test data. For example, the report shown in FIG. 7 lists eight sets of test results under "Bone & Mineral" dating from Jan. 8, 2008 to May 16, 2006 710.

In some embodiments, a report may include information regarding the treatments prescribed to the patient 720. For example, the report may include a set of treatments along with an indication whether the treatment was prescribed at the time the test was taken. Such a report may be generated using the methods and systems described herein. For example, one or more sets of standard-of-care information (such as KDOQI™ guidelines) may be used to identify commonly-prescribed treatments.

FIG. 12 is the Test Results and Treatments section of a Patient Results Report according to a further embodiment. Such further embodiments may include additional information on the report. For example, the report depicted in FIG. 12 includes the patient's CKD stage information as well as date of service 1210. Individuals with skill in the art will recognize that various other relevant information may be provided in various embodiments.

The test results report may be provided to the patient's healthcare provider (e.g., via mail or electronic transmittal).

D. Physician Consultation, Feedback and Patient Support

In some embodiments, Litholink makes its medical director and other physician experts on its advisory board available to physician users free of charge for consultation about the program.

In addition, outcome reports may be sent to physicians at regular intervals e.g., monthly, quarterly, semi-annually, annually, or at any other interval. The outcome reports may compare the progress made by the receiving physician as compared to the rest of Litholink physician users in ameliorating blood and urine chemistry indicators of kidney disease and its co morbidities. In one embodiment, these reports measure the change in the key chemistries as a surrogate outcome.

Figure 12A:
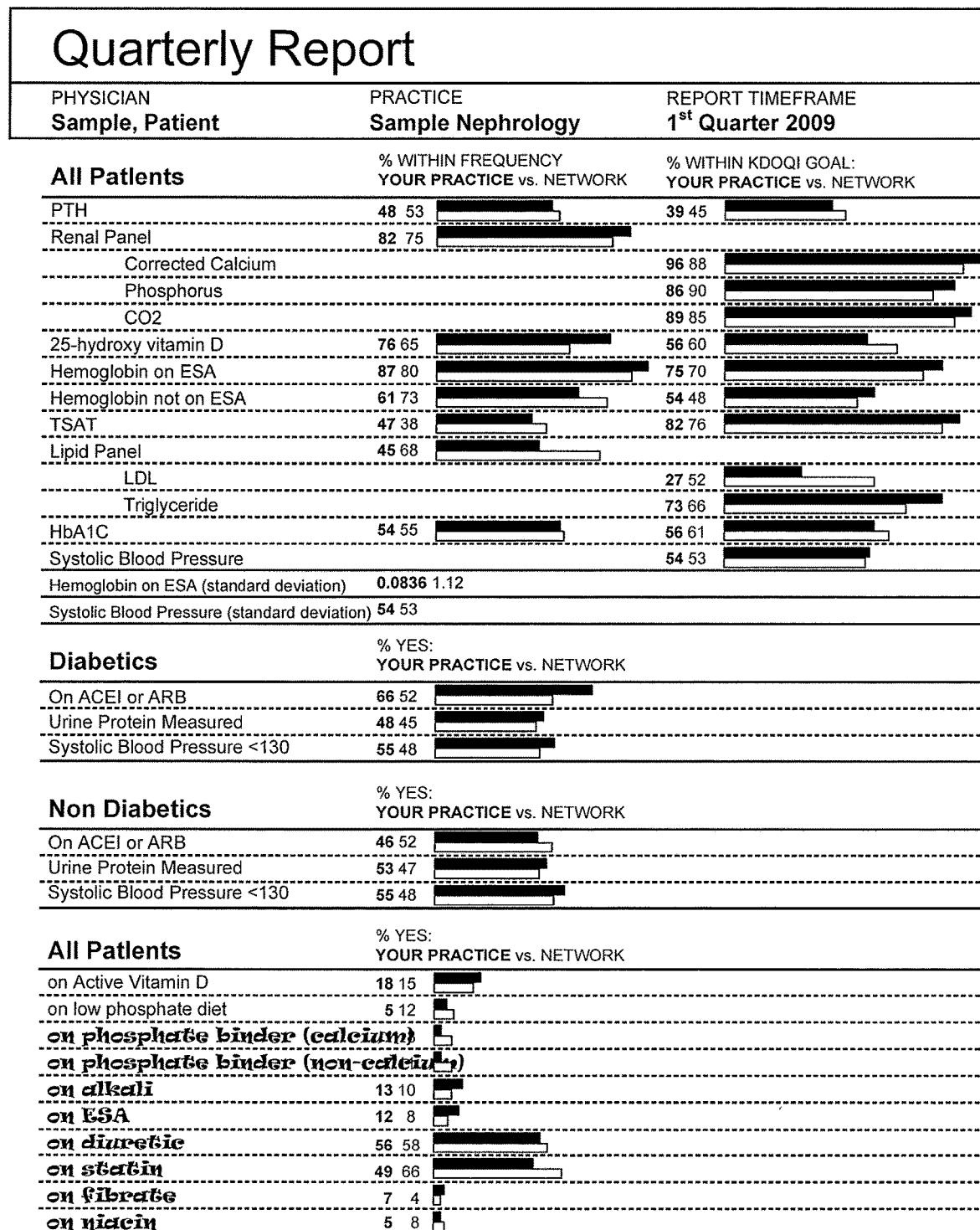

FIGS. 12A, 12B, and 12C depict an outcome according to one embodiment. In one embodiment, depicted in FIG. 12A, the outcome report may provide the percent of measurements made within a range of testing intervals, such as KDOQI's minimum testing frequency intervals, based on stage of CKD for any number of values, including for example, one or more of:

PTH
Calcium
Phosphorus
25-hydroxy vitamin D
Carbon dioxide
Hemoglobin on ESA
Hemoglobin, not on ESA
TSAT
LDL
Triglycerides
Hemoglobin AlC
Systolic blood pressure Also, the outcome report may provide the percent of measurement within a standard, such as a KDOQI goal, based on stage of CKD (if necessary). In some embodiments, this information is displayed graphically. An exemplary embodiment is depictedin FIG. 12A. A benefit is that the graphic representation shows how far each doctor and all doctors as a whole, are within, above or below KDOQI recommended goals. In some embodiments, the graphic image looks like the display on the front page of a Litholink lab results page. Such a report may include information regarding one or more of the following values:

PTH
Calcium
Phosphorus
25-hydroxy vitamin D
Carbon dioxide
Hemoglobin on ESA
Standard deviation of hemoglobin on ESA
Hemoglobin, not on ESA
TSAT
LDL
Triglycerides
Hemoglobin AlC
Systolic blood pressure
Standard deviation of systolic blood pressure In some embodiments, the outcome report may provide information related to the percentage of patients with a particular trait, such as a disease, condition, or medication. This information may be displayed graphically. Examples of how this information is displayed can be found in FIG. 12A. For example, it may show how far each doctor (and/or all doctors as a whole) are within, above, or below one or more recommended goals (e.g., KDOQI recommended goals). In one embodiment, the graphic image looks like the display on the front of a Litholink laboratory results page. In various embodiments the report includes one or more of the following:

Diabetics:
  on ACE/ARB
  with urine protein measured
  with systolic blood pressure <130
Non-diabetics:
  on ACE/ARB
  with urine protein measured
  with systolic blood pressure <130
Person on:
  active vitamin D
  low phosphate diet
  calcium based phosphate binder
  non-calcium based phosphate binder
  alkali
  ESA
  diuretic
  statin
  fibrate
  niacin In some embodiments, the outcome report includes one or more graphs. Six examples of such graphs are shown in FIG. 12B. The graphs may display any information suitable to be displayed in graphical format. For example, the report may include one or more of the following graphs:

Delta Systolic Blood Pressure vs. Initial Systolic Blood Pressure
Delta PTH vs. Initial PTH
Delta LDL vs. Initial LDL
Delta TSAT vs. Initial TSAT
Delta CO2 vs. Initial CO2
Delta Phosphorus vs. Initial Phosphorus
  closed circle: phosphate binder
  open circle: no phosphate binder
  square: on active vitamin D In some embodiments, the outcome report includes a list of patients in need of follow-up tests. An example of such a list is depicted in FIG. 12C. Some embodiments provide a list for each physician of patients in need of follow-up tests within one or more time frames (e.g., three months, six months, twelve months). Some embodiments provide an opportunity for a physician to indicate information. For example, the report may provide the opportunity for a physician to indicate one or more of the following indications regarding a patient: that the patient started dialysis, that the patient had a kidney transplant, that the patient left the care of the physician, or that the patient died.

The Litholink program may also include a patient compliance program in which letters are automatically sent to patients who have not complied with a physician's order, e.g., failed to get blood drawn or urine collected. In one embodiment, the Litholink program sends lists of patients to physicians that have not had follow-up after therapy has been initiated. Diet and other patient education materials from the National Kidney Foundation are also provided by Litholink to patients.

System Architecture According to One Embodiment

Figure 13:
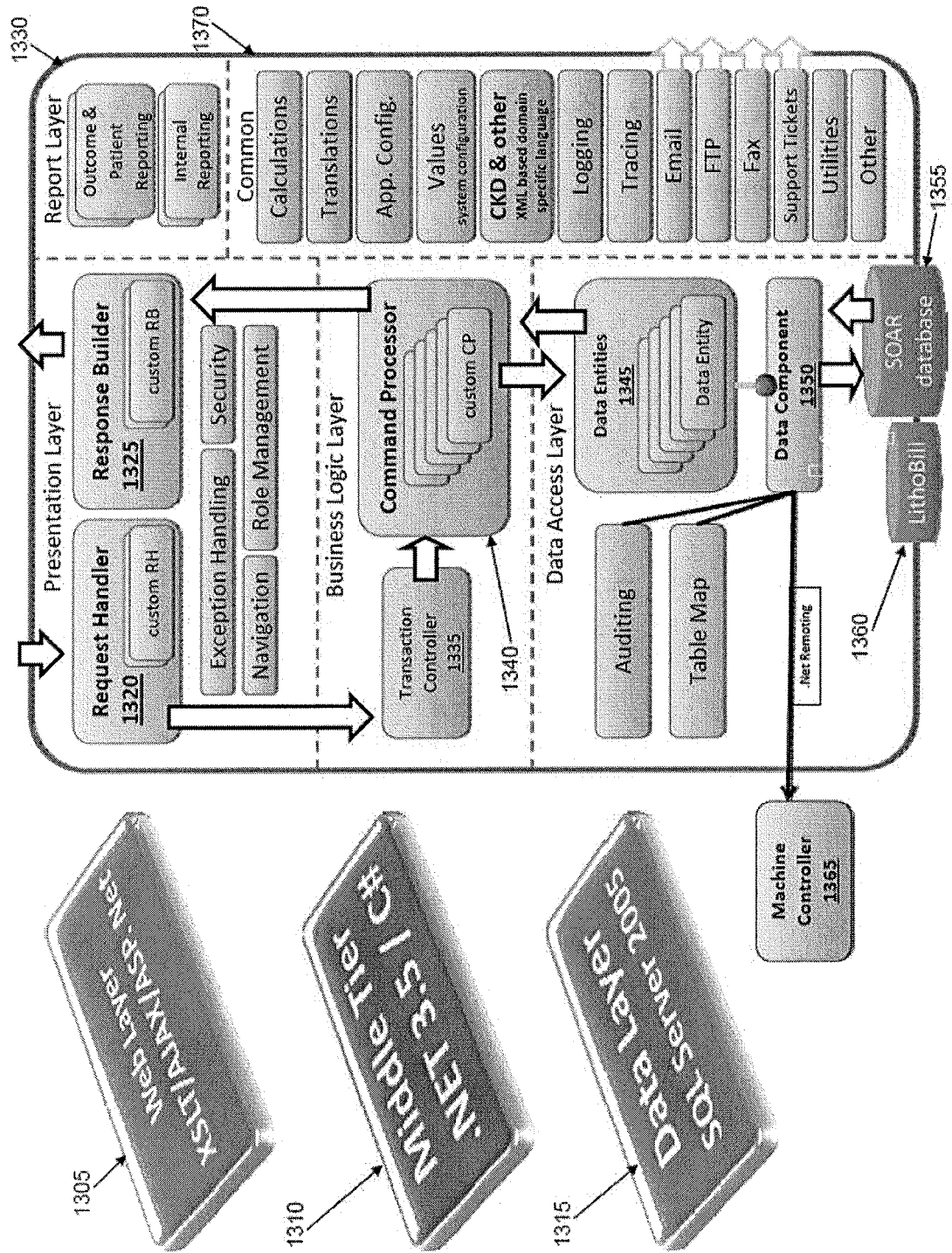
FIG. 13 depicts the functions handled by the various components of the SOAR architecture, according to one embodiment.

In some embodiments, the systems and methods described herein may be executed on a computer-based architecture. An example is SOAR, which is an N-Tier, open architecture, component-based software system using the C# programming language, Microsoft SQL Server 2005 and XML technology. FIG. 13 depicts the functions handled by the various components of the SOAR architecture, according to one embodiment.

In one embodiment, the SOAR architecture includes three tiers. The first tier is the Web Layer 1305. The Web Layer 1305 may utilize such technologies as XSLT, AJAX, ASP-.Net, and/or other suitable technologies known in the art. A second tier is the Middle Tier 1310. The Middle Tier 1310 may utilize such technologies as .Net and C#. In other embodiments, the Middle Tier 1310 may use various other platforms, such as WebSphere. A third tier is the Data Layer 1315. The Data Layer 1315 may utilize Microsoft SQL Server technology. In other embodiments, the Data Layer 1315 may utilize any other suitable database technology known in the art, such as Sybase, Oracle, or DB2.

A. Web Layer

Figure 15:
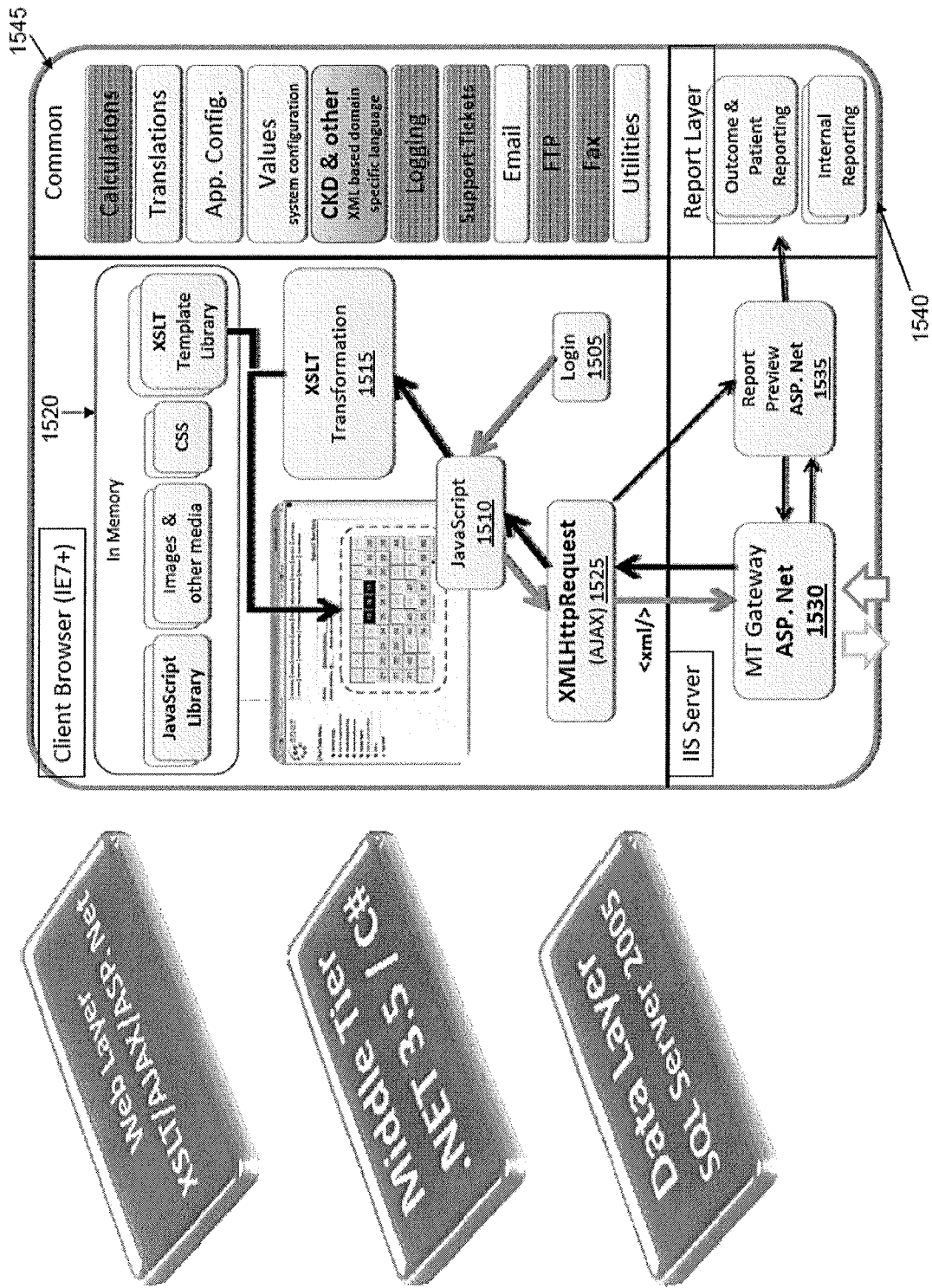
FIG. 15 depicts the interaction between software components according to one embodiment.

In some embodiments, the Web Layer in FIG. 15 includes a User Interface (UI) layer. The UI layer may reside on a server, such as, for example, a server running IBM WebSphere or Microsoft's Internet Information Services. The server may communicate to the Presentation Layer through the Middle Tier gateway 1530. The Web Layer may communicate through a web browser, such as Internet Explorer, Mozilla Firefox, or other browser technology. In some embodiments, the communication takes place using one or more of: the native XMLHttpRequest object, JavaScript, XSLT, AJAX, or any appropriate syntax technology known in the art that is capable of generating from the SOAR XML different types of output. The output may include one or more of: HTML, Silverlight objects, or any other appropriate format known in the art, such as XML, email, plain text, PDF, or others.

B. Middle Tier

Some embodiments include a Middle Tier 1310. The Middle Tier 1305 may include a Presentation Layer (also known as a service layer). The Presentation Layer may include a Request Handler 1320. The Presentation Layer may include a Response Builder 1325.

In some embodiments the Request Handler 1320 is a software program executable on a computer. The Request Handler 1320 may receive data representing a request. The Request Handler 1320 may perform tasks including one or more of the following: exception handling, navigation, security, and role management.

In some embodiments, the Response Builder 1325 is a software program executable on a computer. The Response Builder 1325 may perform tasks including one or more of the following: exception handling, navigation, security, and role management. The Response Builder 1325 may provide information responsive to a request. The response may be in any appropriate format known in the art, such as XML, HTML, email, plain text, PDF, or others.

In some embodiments, the Middle Tier 1305 includes a Report Layer 1330. The Report Layer 1330 may include any number of types of reporting functionality. For example, the Report Layer 1330 may include outcome reporting and/or patient reporting. In some embodiments, the Report Layer 1330 includes internal reporting. The reports provided by the Report Layer 1330 may be in any appropriate format known in the art, such as XML, HTML, email, plain text, PDF, or others.

The Middle Tier may include a Business Logic Layer. The Business Logic Layer may include one or more software programs executable on a computer. The components of the Middle Tier 1310 may reside on a different computer (or set of computers) as the components of the Web Layer 1305. Or they may reside on the same set of computers. In other embodiments, there may be an overlap, such that some components of the Web Layer 1305 may reside on the same computer(s) as some components of the Middle Tier 1310.

The Business Logic Layer may include a Transaction Controller 1335. The Transaction Controller 1335 may receive data, such as request data, from the Request Handler 1320. The Transaction Controller 1335 may perform operations on the data it receives. For example, the Transaction Controller 1335 may perform formatting on the request. In some embodiments, the Transaction Controller 1335 may route the request to a Command Processor 1340 or other system for processing.

In some embodiments, the Business Logic Layer includes a Command Processor 1340. The Command Processor 1340 may receive a request from the Transaction Controller 1335. In some embodiments, the Command Processor 1340 performs one or more operations in response to the request. In some embodiments, there are one or more custom Command Processors. These custom Command Processors may operate for processing certain types of requests and/or commands.

C. Data Layer

Some embodiments include a Data Layer 1315. The Data Layer may include a Data Access Layer. The Data Access Layer may include one or more software programs executable on a computer. The components of the Data Layer 1315 may reside on a different computer (or set of computers) as the components of the Web Layer 1305 and/or the Middle Tier 1310. Or they may reside on the same set of computers. In other embodiments, there may be an overlap, such that some components of the Web Layer 1305 may reside on the same computer(s) as some components of the Middle Tier 1310 and/or some of the components of the Data Layer 1315.

In some embodiments, the Data Layer 1315 comprises a database, such as SQL Server provided by Microsoft, DB2 provided by IBM, or Oracle Database provided by Oracle Corporation. Some embodiments include one or more Data Entities 1345. The Data Entities may receive commands from a Command Processor 1340. Further, the Data Entities may communicate with one or more Data Components 1350. The Data Components 1350 may include an auditing functionality and/or a table map.

In some embodiments, the Data Components 1350 may communicate with a database, such as the SOAR Database 1355. The SOAR Database 1355 may be any database known in the art, such as those described herein. The SOAR Database 1355 may include information related to standard-of-care, such as KDOQI™ data. The SOAR Database 1355 may also include historical test data. In various embodiments, the SOAR Database 1355 includes various types of data necessary to generate laboratory reports as described herein. In some embodiments, the SOAR Database 1355 is in communication with one or more additional systems, such as a billing system 1360. In some embodiments, the Data Component 1350 is in communication with a Machine Controller 1365.

In some embodiments, the Middle Tier 1310 and Data Layer 1315 have one or more common features 1370. These common features may include one or more of the following: performing calculations, performing translations, configuring the application, configuring the system, operations related to a domain-specific language, logging, tracing, email, FTP, fax, operations related to support tickets, or various utilities.

Web Software Infrastructure According to One Embodiment

As discussed herein, some embodiments may be executed on a computer-based architecture such as SOAR, which is an N-Tier, open architecture, component-based software system using C#, SQL server 2005 and XML technology. FIG. 14 depicts an ADO.NET software architecture that can be used to provide the application with access to the data stored in a database, according to one embodiment.

In one embodiment, a set of computer components is provided to allow applications, such as those that create the laboratory reports described herein, to access data and data services. One such set of components is the ADO.NET architecture provided by Microsoft Corporation. ADO.NET provides a set of classes that allow application programmers to access data in a database such as Microsoft SQL Server or Oracle database.

In some embodiments, the ADO.NET framework 1410 is used to provide access to data. For example, the application containing logic for generating laboratory reports may utilize ADO.NET classes to access data necessary to make its calculations. The ADO.NET classes may pull data from the database and store it in a DataSet object, which functions similarly to a relational database. When the DataSet object is populated, the application can perform operations on data stored therein, rather than requesting it from the database. This can have benefits such as speed and efficiency.

The ADO.NET framework 1410 may have access to data stored in one or more tables 1420. In addition, the ADO.NET framework 1410 may have access to one or more functions 1430. Further, the ADO.NET framework 1410 may have access to one or more views 1440. Also, the ADO.NET framework 1410 may have access to one or more stored procedures 1450. Additionally, the ADO.NET framework 1410 may have access to one or more extended stored procedures 1460.

In various embodiments, one or more software components are included. FIG. 15 depicts the interaction between software components according to one embodiment. In the embodiment depicted in FIG. 15, a user logs into a web-based system 1505. The user may be a patient, medical provider, insurer, or other entity. In various embodiments, the information presented to the user varies based upon who the user is.

Various components may be used in order to provide the information to the user in a particular form. In one embodiment, a web scripting language such as JavaScript 1510 is used to perform logical functions in connection with requests made by the user. The JavaScript code 1510 may interact with a Extensible Stylesheet Language Transformations (XSLT) filter 1515 that enables XML documents to be transformed into a different format. The XSLT filter 1515 may interact with one or more utilities 1520, such as an XSLT template library, one or more cascading style sheets (CSS), images and other media, and a JavaScript library. In some embodiments, one or more of the components herein mentioned work together to provide information to the user.

The information provided to the user may take a variety of forms. For example, the information may include options from which the user may select. If a user selects an option, such as to produce a particular report, additional components may come into play. For example, the JavaScript code 1510 may interact with a web application such as an Asynchronous JavaScript and XML (AJAX) utility 1525. In some embodiments, the JavaScript code 1510 executes an XMLHttpRequest call 1525 in order to send a request to a web server. The XMLHttpRequest call 1525 may serve to request data from the server and load the response back into the scripting language (e.g., JavaScript).

The XMLHttpRequest call 1525 may communicate with a web server, such as IBM WebSphere or Microsoft's Internet Information Services (IIS). In one embodiment, an IIS server is used for the web server. In one embodiment, an ASP.NET application 1530 is running on the IIS server. The ASP.NET application 1530 may receive the request from the XMLHttpRequest call 1525. Further, the ASP.NET application 1530 may retrieve the data requested and provide it to the XMLHttpRequest call 1525, which provides it to the JavaScript code 1510. In some embodiments, the XSLT filter 1515 as well as other relevant utilities 1520 are used to format and present the data.

In some embodiments, the ASP.NET application 1530 interacts with a Report Preview application 1535. The Report Preview application 1535 may also be an ASP.NET application. In some embodiments, the Report Preview application 1535 is executed on the IIS server. The Report Preview application 1535 may interact with other utilities in the Report Layer 1540.

The Report Layer 1540 has one or more functions in various embodiments. For example, the Report Layer 1540 may include outcome and patient reporting. In some embodiments, the Report Layer 1540 includes internal reporting. As will be apparent to those of skill in the art, various types of reporting may be provided in different embodiments.

Figure 16:
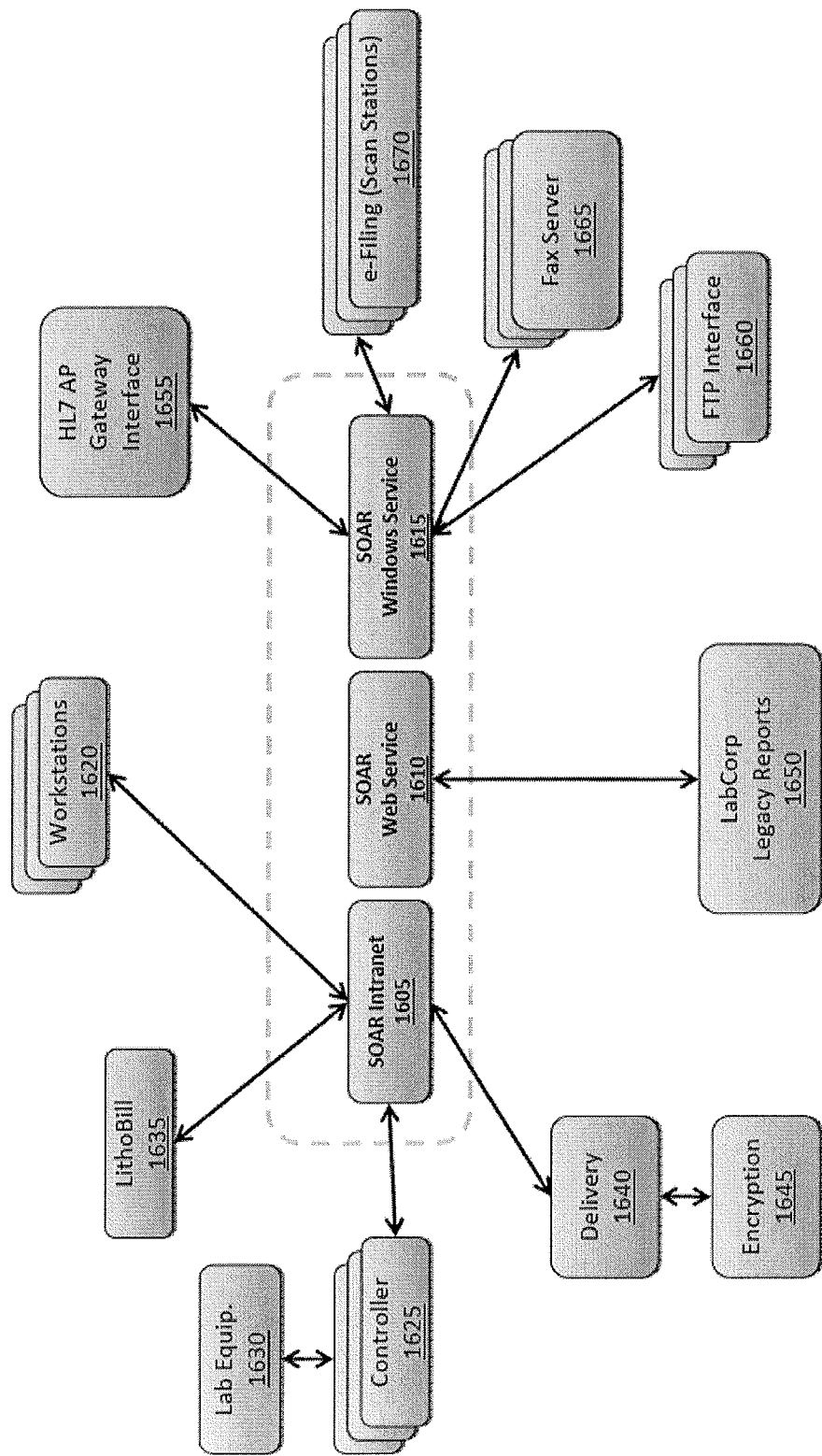
FIG. 16 depicts the Litholink application infrastructure according to one embodiment.

Some embodiments include common features 1545 that may be shared by one or more components. These common features 1545 may include one or more of the following: performing calculations, performing translations, configuring the application, configuring the system, operations related to a domain-specific language, logging, email, FTP, fax, operations related to support tickets, or various utilities.
Application Infrastructure According to One Embodiment In some embodiments, an application is provided. The application may leverage the SOAR framework described herein. One example of such an application is the Litholink CKD application provided by Litholink Corporation. FIG. 16 depicts the Litholink application infrastructure according to one embodiment.

In some embodiments, the Litholink application utilizes one or more SOAR components. For example, the Litholink application may utilize the SOAR Intranet component 1605. In one embodiment, the Litholink application utilizes the SOAR Web Service component 1610. In one embodiment, the Litholink application utilizes the SOAR Windows service component 1615. In various embodiments, the Litholink application may utilize one, both, or all three components.

A. SOAR Intranet

In one embodiment, the Litholink application utilizes the SOAR Intranet component 1605. There may be one or more workstations 1620 capable of providing access to the SOAR Intranet 1605. The workstations 1620 may be used to interact with components of the SOAR Intranet 1605. The interaction may take place as described in connection with the discussion of FIG. 15, herein.

One embodiment includes a Machine Controller 1625 and one or more pieces of Lab Equipment 1630. The Machine Controller 1625 may communicate with one or more components of the SOAR Intranet 1605. The Machine Controller 1625 may also communicate with the Lab Equipment 1630. The Lab Equipment 1630 may include any type of hardware used to test a specimen. In one embodiment, a component of the SOAR Intranet instructs the Machine Controller 1625 to provide data from the Lab Equipment 1630. The Machine Controller 1625 is communicatively connected to the Lab Equipment 1630 via a wired or wireless connection in order to send and receive instructions and data.

In some embodiments, a billing software is also used. In the Litholink application the billing software is LithoBill 1635. LithoBill 1635 may be communicatively connected to one or more components of the SOAR Intranet 1605. LithoBill 1635 may have access to data collected and provided by SOAR Intranet 1605.

In some embodiments, information such as reports (e.g., outcome reports), bills, or other communication, is provided to users. One way this can be done is via email delivery 1640. Other means, such as fax, instant message, or any other known communication means may be used. Because this information is often sensitive, encryption may be used to secure the communication. In one embodiment, ZixCorp encryption 1645 is used.

B. SOAR Web Service

According to the Worldwide Web Consortium, a Web Service is "a software system designed to support interoperable machine-to-machine interaction over a network. It has an interface described in a machine-processable format (specifically WSDL). Other systems interact with the Web service in a manner prescribed by its description using SOAP-messages, typically conveyed using HTTP with an XML serialization in conjunction with other Web-related standards."

In some embodiments, a SOAR Web Service 1610 is provided. The SOAR Web Service may be used to provide reports. For example, it may be used to provide LabCorp Legacy Reports 1650. These reports may be provided to users in any way known in the art, e.g., via a HyperSend interface.

C. SOAR Windows Service

A Windows Service is a process that runs on a computer running the Microsoft Windows operating system that performs one or more specific functions and is typically designed not to require user interaction. Often Windows Services are executed upon startup and run until the computer is shut down. Windows Services are analogous in some ways to a Unix daemon process. Sometimes Windows Services are referred to as "background" processes.

In some embodiments, a SOAR Windows Service 1615 is provided. The SOAR Windows Service 1615 may allow various systems to interact with it. For example, an HL7 AP Gateway Interface (EDI interface to LabCorp or other electronic medical record providers) 1655 may interact with the SOAR Windows Service 1615. Additional systems that may interface with the SOAR Windows Service 1615 include one or more of: an FTP Interface 1660, a Fax Server 1665; and one or more e-Filing Scan Stations 1670.

A Patient Data Flow According to One Embodiment

Figure 17:
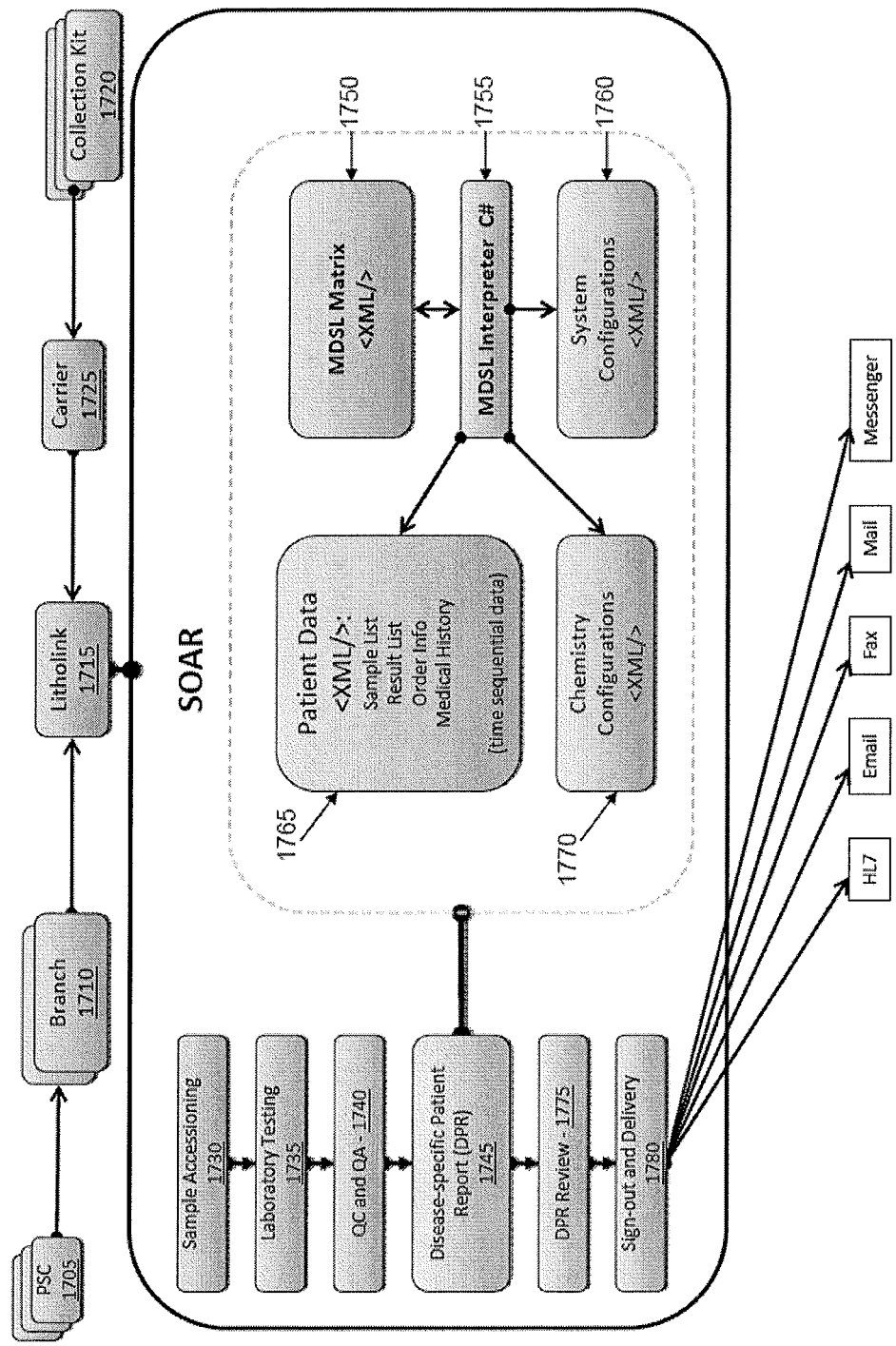
FIG. 17 depicts a patient data flow according to one embodiment.

In some embodiments, a patient provides a specimen to an entity such as Litholink or LabCorp, and a report, such as a Disease-Specific Patient Report (DPR) is produced as a result. FIG. 17 depicts a patient data flow according to one embodiment.

In order to produce a report, such as a DPR, the patient first provides a specimen. In one embodiment, the patient provides a specimen to a Patient Service Center (PSC) 1705. The PSC 1705 then provides the specimen to a laboratory location, such as a LabCorp Branch 1710. The LabCorp Branch 1710 may perform one or more tests on the specimen. In one embodiment, the LabCorp Branch provides the specimen and/or data related to the specimen to another location, such as Litholink 1715.

Alternatively, the patient may be provided with a collection kit 1720 in order to collect and provide his/her own specimen. In one embodiment, a CKD kit is provided, the contents of which are listed in Table 1. A benefit to this method is that the patient is not required to visit a PSC in order to provide the specimen. The patient may then provide the specimen to a provider 1715 such as Litholink via a carrier 1725 such as Fedex, UPS, or any other entity capable of transporting a specimen.

TABLE 1

CKD Kit Contents

CKD Patient Sample Shipping Box
Foam cooler
Biohazard big
Absorbent pad
1-2 Cold packs
FedEx shipping label
Patient Test Forms
Phlebotomist Instructions
Sticker of bank to seal foam cooler
Lavender Top (EDTA) Tube
Gold Top (SST) Tube
White TOP (PPT) Tube
Orange Top Spot Urine Tube According to one embodiment, when the provider 1715 receives the specimen it utilizes the SOAR infrastructure in order to process the specimen. In one embodiment, the specimen is accessed 1730 in order to begin processing. The specimen may take on a variety of forms, e.g., blood, urine, or others. The form of the specimen plays a role in determining how to handle the testing results from the specimen.

After accessioning the specimen 1730, the specimen is tested 1735. In various embodiments, any number and/or type of tests may be run on the specimen. Running the tests 1735 generates data related to the specimen. The data may include data such as the amount of glucose in the sample, the amount of creatinine in the sample, the red cell count, and/or any number of other values.

In some embodiments, quality control and/or quality analysis is performed 1740. Due to the critical nature of the test data, it is important for the data to be accurate.

For various testing panels the physical testing and test result quality control may be handled by a testing facility, such as a LabCorp branch. In some embodiments, the raw outcome data is transmitted via HL7 to Litholink's SOAR servers. Disease-specific interpretation and additional quality control will take place thereafter.

In some embodiments, after the test data is generated 1735 (and QC/QA 1740 is performed, if necessary), a DPR is generated.1745. In order to create a DPR, the data is interpreted. In various embodiments, the data may be interpreted in a variety of ways. In one embodiment, a Medical Domain-Specific Language (MDSL) is used.

In one embodiment, a MDSL Matrix 1750 is utilized. As described herein, a matrix structure provides an effective and efficient way to evaluate the numerous conditions associated with the test results. A MDSL Interpreter 1755 may also be used. In one embodiment the MDSL Interpreter 1755 is a software program that understands the MSDL Matrix and protocol and drives the analysis of the patient related time-sequential outcome data and previous interpretations. Interpretations by the interpreter rely on the MDSL Matrix 1750 and system wide configurations 1760 about settings, such as one or more of: chemistries, cut-points, reference ranges, or other settings. Further, the MDSL Interpreter 1755 may communicate with the MDSL Matrix 1750. In some embodiments, the MDSL Interpreter 1755 requests and receives the medical protocol data from the MDSL Matrix 1750 and time sequential test data from the patient data 1765. Other information from KDOQI™, ATP III or other standard-of-care sources is embedded in the medical protocol of the MDSL Matrix 1750.

In some embodiments, the MDSL Interpreter 1755 provides Patient Data 1765. The Patient Data 1765 may be in XML format. It may include such information as a sample list, a result list, order information, medical history, or other relevant information. Other data provided to the MDSL Interpreter 1755 may include Chemistry Configurations 1770. These may also be in XML format. The Patient Data 1765 and Chemistry Configurations 1770 may be used to create a DPR.

After the DPR is created 1745, it may be reviewed 1775. The review may be for quality control purposes. Due to the critical nature of the information contained in a DPR, it is important for it to be accurate.

After the DPR has been created 1745 and reviewed 1775, it may be provided 1780. In some embodiments, a system is provided for the DPR to be signed out and delivered 1780. The DPR may be delivered in any number of ways, such as in HL7 format, via email, via fax, via postal mail, via instant messenger, or in any other way known in the art.

A Patient-Specific Treatment Options Software System According to One Embodiment A. Options for Treatment In some embodiments, the "treatment options" shown in the patient results reports at FIGS. 5-6 and 10-11 are produced by a software system containing algorithms which are able to direct a computer's search for the correct option for treatment for the specific patient from multiple data bases, taking into account that patient's prior test results, demographic information, and treatments. The medical advice may be based on a set of guidelines, such as those established over several years in a process created and managed by the National Kidney Foundation (NKF) specifically to gather and recommend best CKD treatment practices from data in the scientific literature and from experts in CKD. The NKF's KDOQI™ convened panels of experts in CKD and related fields and produced 12 clinical practice guidelines for the five stages of chronic kidney disease, its complications and co-morbidities. The KDOQI™ guidelines are recognized by leading public health authorities and medical societies as the most comprehensive and authoritative guide to CKD treatment.

For its treatment recommendations on cardiovascular disease related to CKD, in one embodiment, treatment options are based on the guidelines initiated by The National Heart, Lung and Blood Institute of the National Institutes of Health and developed in the "Third Report of the National Cholesterol Education Program Expert Panel on Detection Evaluation and Treatment of High Blood Cholesterol in Adults" (ATP III). In a limited number of areas of CKD treatment where the KDOQI™ or ATP III guidelines are incomplete, experts, such as those from a national panel of experts convened by Litholink, may provide the treatment suggestion. An example of such a national panel of experts may include the National Expert Advisory Panel on CKD, which is represented by Table 2, but the experts' names have been replaced by hypothetical names.

TABLE 2

CKD Board Member Scientific Advisory Board

| | |
|---|---|
| John Doe, MD<br>Medical Director, Litholink<br>Laboratory Corporation of America<br>jdoe@domain.com | John Public<br>Chief Executive Officer,<br>Laboratory Corporation<br>of America<br>jpublic@domain.com |
| Perry Mason, MD<br>Professor, Adult and Pediatric<br>Endocrinology, Diabetes, Metabolism<br>Department of Medicine, University<br>of Chicago Pritzker School of<br>Medicine<br>Chicago, IL<br>pmason@domain.com | Florenz Meyer, MD<br>Professor, Division of<br>Nephrology, St. Paul's Hospital,<br>University of British<br>Columbia, Vancouver, Canada<br>fmeyer@domain.com |
| Travis McGee, MD<br>Chief of Clinical Research, Denver<br>Nephrology, Associate Clinical<br>Professor Medicine, University of<br>Colorado Health Sciences Center,<br>University of Colorado, Denver,<br>Colorado<br>tmcgee@domain.com | Della Street, MD<br>Chief Executive Officer, Litholink<br>Vice President, Laboratory<br>Corporation of America<br>dstreet@domain.com |

Using an embodiment of the invention may improve the quality of care of chronic kidney stone patients. Although treatment guidelines from KDOQI™ and ATP III are posted on the official guideline site of the National Guideline Clearinghouse of the Agency for Health Research and Quality (AHRQ), they consist of hundreds of pages of lengthy and complex narratives and are not conveniently usable at the point of care for most physicians, particularly primary care physicians. Kidney disease is highly complex and each patient presents different variables affecting treatment. It has long been acknowledged that physicians need uniform evidence based guidelines for care and computerized decision support to implement them. They need their specialty's guidelines sorted out and presented in patient relevant terms at the point of care.

B. Summary of the Construction of the Treatment Option Software Program

In some embodiments, the Litholink software is able to produce patient-specific treatment recommendations through the use of linked matrix trees written in XML that simultaneously interrogates entire grids of logic for different CKD diseases, treatments and results. Test results may be evaluated by the system based on one or more of three key inputs: (1) whether test results are below, within or above KDOQI™ or ATP III guidelines, (2) whether medication is being used and (3) whether test results have changed from prior test results in a material way. In some embodiments, short, substantive medical content "tags" of narrative advice are condensed from the guidelines for the software matrix which then pulls the relevant tags for the specific patient condition. Cross-references and the testing of other conditions, made possible by this syntax, may make the tags complete, intelligent, and medically accurate.

In one embodiment, a logical if-then-else or switch statement arrangement is used. In another embodiment, a matrix approach is used in constructing the program. In one embodiment, the matrix approach interrogates multiple conditions at once, allows for the call of additional sub-matrixes, and uses its own short-hand language to reference conditions and tests outside the matrix. A benefit of the matrix approach is increased speed and programming efficiency.

In one embodiment, the entire syntax is driven by extensible markup language (XML). The medical information matrix and logic is not embedded within the software code. The software code utilizes a domain-specific language developed by Litholink for the medical community. In one embodiment, the domain-specific language is embedded in Litholink's protocol. The XML document feeds the software and can be extended without additional compilation of the program. Medical instructions may be built by tags, which represent segments within the XML document. The segments have instructions about KDOQI™ references, follow-up measurements, timeframes, and the actual representation of the text displayed in the final outcome report.

C. Specific Components of the Software System

1. Matrix Logic

Figure 18:
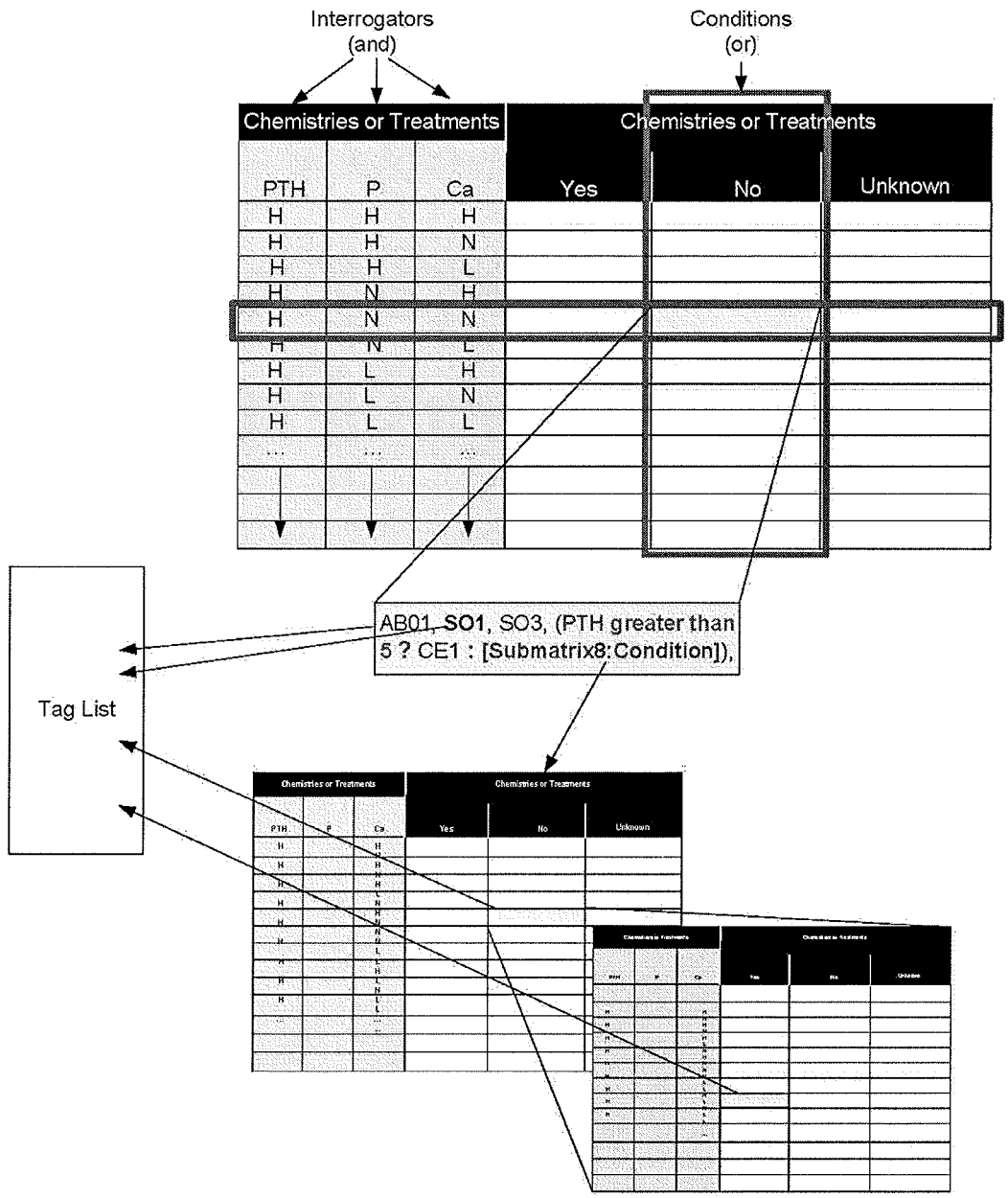
FIG. 18 depicts an illustration of an example of the matrix logic according to one embodiment.

In one embodiment, the matrix syntax uses a structured approach of interrogating conditions, responses, time-sequential data or other defined medical information. FIG. 18 provides an illustration of an example of the matrix logic. Any matrix block allows the software to cover every possible permutation for the condition in question. It allows the system to query sub matrixes infinitely and to cross reference. The software code is completely separated from the medical instruction. The following is specific to one embodiment of the Litholink CKD matrix:

a. Domains

The CKD matrix is separated into medical domains. The domain order defines the output order. Each domain has primary chemistries, which are needed for the interpretation and are represented individually. Changes to previous testing are recorded and evaluated.

b. Paragraph

Each paragraph segment is handled like an individual object. The outcome is stored and tracked by the system. Segment order, follow-up measurements and timeframes are prioritized by the matrix.

c. Matrix

The matrix syntax is developed in C# code in conjunction with a domain specific programming language embedded into the Litholink XML matrix protocol. The domain-specific language, special tests, calculations, instructions, and short hand syntax are interpreted in the software. The matrix language and paragraph text are stored in the XML matrix. The matrix structure is defined within the matrix itself to enable self-awareness and flexible expansion at any time. The matrix query, to allow the interrogation of multiple conditions at once, is driven by XPath (XML query syntax) in conjunction with C# (Microsoft .Net framework, version 2.0, 3.0, etc.). Chemistry results, normal ranges (also known as reference intervals) and condition evaluations are based on Litholink's SOAR framework. SOAR is Litholink's proprietary software framework managing the entire IT infrastructure from patient call questionnaires, management reporting, billing, to laboratory information solutions.

2. Matrix Protocol

In one embodiment, Litholink's medical matrix protocol is defined as an XML structure. For this documentation, the structure of nested nodes is visualized with the help of Altova® XMLSpy®'s grid view (see below). Litholink's medical matrix protocol may use the namespace "xmlns:LL="http://www.litholink.com/dsl" for the CKD program. A xsd schema was defined for the protocol in one embodiment of the invention.

A Protocol Overview is illustrated in FIG. 19.

a. Active Domain List

In one embodiment, the Active Domain List (LL:ActiveDomainList) defines the domain nodes (LL:Domain) to be used actively for the medical protocol. The Active Domain List, along with the identification as described below, is shown in FIG. 20. The following domain nodes are defined in one embodiment of the invention:

1. Disease ID: The Disease ID (DiseaseID) defines for our framework the disease (condition) the patient is evaluated for. All outcome matrix results are stored separately by disease.

2. Active Domain: The Active Domain (ActiveDomain) lists one or more active domains by its "Type" name in the LL:Domain node. The active domain is the entry point for the protocol to investigate samples. It is the entry point of its self-awareness (see explanation above; more details under "Matrix" and "Sub Matrix" below).

b. Domain

In one embodiment, the domain is identified in the active domain list. The identification is shown in FIG. 20.

1. Type: Each domain called by the active domain list (see above) has a "Type" identifier.

2. Sample Type: Patients have different types of samples brought to us as a laboratory. Sample types could include (urine, serum, spot urines, etc.). Each medical domain interrogates similar chemistries, measurements, or other order information. The basic sample type is defined for each domain. Unless specified in the domain-specific language or protocol the chemistries default for each domain to this sample type.

3. Assessment List

The assessment list (AssessmentList) defines the components, which are listed and investigated in the assessment paragraph of our outcome reporting. The Assessment node lists the chemistry. Each chemistry shows a value display definition and whether the value has changed over time and is within the medical guidelines (cut points for the guideline and the guideline types are defined for each chemistry in our SOAR framework definitions.) The reported value (ReportedValue) lists information gathered from the physician office or other medical facility, which are submitted in any number of ways, such as via order form or electronic records (HL7). The reported values are used in conjunction with chemistries and determine the outcome reporting, hence reporting back these values are essential. An assessment list is shown in FIG. 21.

4. Additions (Overrides)

In one embodiment, "additions" are additional or overriding sentences which are unique, depend on one significant medical condition only, or are true for every situation. Each overriding or additional "Sentence" is interrogated for each paragraph types (Type). There are currently three paragraph types or parts: "Assessment", "Treatment", and "Follow-Up". The "Position" may determine whether the sentence should appear at the beginning or the end of the paragraph part. The "Tag" may define additional segments to be called for the "Treatment" section (see more details and triggers handled by the segments below). The "Condition" may be the interrogating condition, which is optional. The condition has to be fulfilled in order to trigger the "Tag" to be added and/or the "Text" to be added to the paragraph part (see "Conditions & Domain-specific language" for more details about the condition evaluation). Additions are shown in FIG. 22.

5. Follow Up (Definitions)

In one embodiment, follow-up definitions are unique for each domain. This part of the protocol may describe the time frame for individual follow-up commands, which are called in the "Segment List" or the "Additions" section. The "Tag" may identify the timeframe. In one embodiment, "Desc" describes in English the words for the outcome report, which apply to the called timeframe. "Weeks" may define for the system the exact time as a measurable value. Follow Up Definitions are shown in FIG. 23.

In one embodiment, "Measurement" describes the panel type which is called with the timeframe (ex. "M5-T1"=CBC is due now). "Tag" may identify the measurement. "KDOQI™" indicates whether this was a guideline-specific panel. "PrimaryChemistry" identifies one chemistry from the given panel. Setting the "primary chemistry" may allow the system to check whether the panel was tested completely. In one embodiment, the SOAR framework ensures through our quality assurance process that all chemistries are reported together in one panel. Checking one primary chemistry may indicate the entire panel is present. "Desc" may describe in English (or another language) the words for the outcome report.

6. Segment List

In some embodiments, the segment list contains one or many segments specific for the medical domain. A segment list and segments are shown in FIG. 24.

7. Tag Identifier

In some embodiments, the segment has a "Tag" identifier, which is unique within the domain. "KDOQI™" identifies whether the instruction in the "Text" node is guideline-based or not. "Measurement" may contain the domain-specific language (DSL) for Litholink's matrix protocol. Though primarily used to identify measurements and timeframes (see Follow-Up for details), the syntax could trigger other segments and condition interrogations (see "Conditions & Domain-Specific Language (DSL)" for details). "Text" is the information that may be added to the outcome report paragraphs.

8. Matrix

Figure 25:
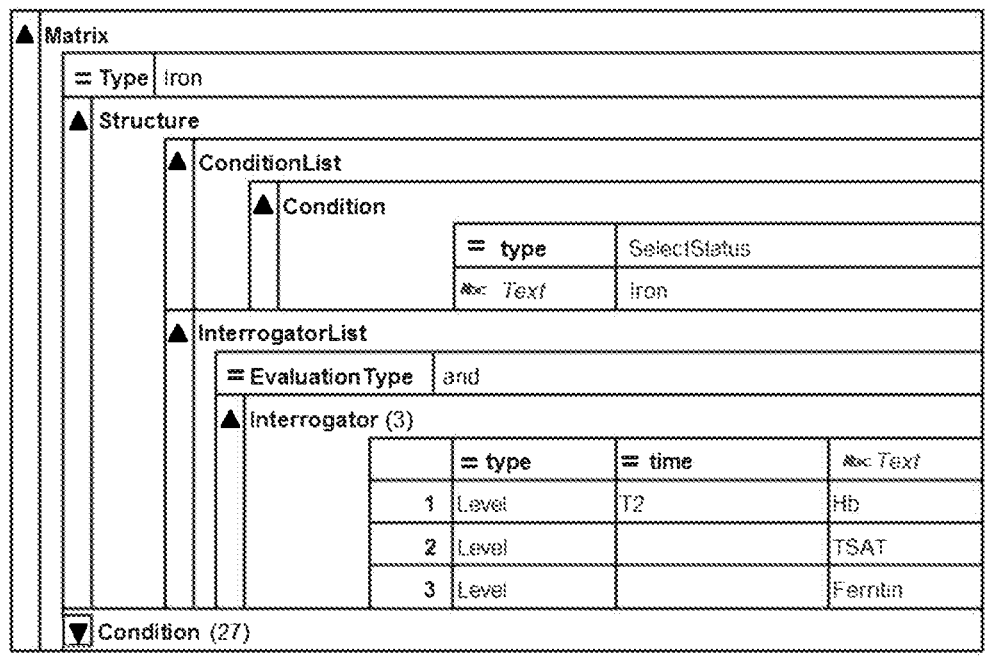

In some embodiments, "Type" in the Matrix node uniquely identifies the matrix within the structure. A matrix is shown in FIG. 25. The following elements are described in accordance with one embodiment of the invention:

a. Structure:

"Structure" defines the matrix layout. The structure identifies for the software language (DSL), what interrogation and condition syntax to build. The syntax is built in form of the XPath query language to select the XML nodes, which contain DSL instructions (see "Conditions & Domain-Specific Language (DSL)" for more details). The "Condition List" defines the all XML elements and their condition description. Condition "types" are "SelectStatus" or "Level". "Select Status" defines whether a order form information was selected with "Yes", "No", or "Missing" (=Unknown). "Level" refers to "H" (=High), "N" (=Normal), "L" (=Low), or "U" (=Unknown/not present). For example the following condition definition "<Condition type="SelectStatus">Statin</Condition>" tells the system to look for a xml node "Statin_yes", "Statin_no", or "Statin_unknown" based on what the physician or nurse told Litholink on the order form. The attributes for this XPath query, to select the correct node in the matrix, is defined in the "Interrogator List".

"Interrogator List" makes the matrix protocol a powerful and flexible solution. The list contains one or many Interrogators, which define the chemistry or order form information based on its type. Current types available are "SelectStatus", "Level", "Evaluation", "Delta", and "DeltaRate". "Select Status" and "Level" are explained above. "Evaluation" has a "condition" attribute defined in the "Interrogator" node. This allows a condition to be medically evaluated and the result could be "Yes" or "No". "Delta" defines the difference between the current minus the last result for the given chemistry and identifies whether the result is "Increased", "Unchanged", or "Decreased". "DeltaRate" interrogates the same outcome however the delta rate is defined per chemistry over a given time frame only.

Interrogators are concatenated by either an "or" or "and" "Evaluation Type".

The Structure tells the system what chemistries to interrogate and how to build the query XPath syntax to identify the correct xml element, which contains the DSL syntax to build a outcome report.

b. Condition

"Condition" contains the actual matrix with attributes and elements, which result in additional sub matrix calls (see details below) or DSL interpretations.

For example: If a patient has a high $CO^2$ and low K (potassium) value and the physician told us, the patient currently takes "Alkali" medication, the program knows to the syntax "K4,K5". The exact meaning of this syntax is described below.

The amount of conditions, attributes, and elements are absolutely flexible and depend on the way a physician was trained to investigate symptoms and other medical factors.

9. Sub Matrix

In some embodiments, the sub matrix has the identical structure as "Matrix". It may contain the "Structure" and "Condition" element. The sub matrix may be used to interrogate further from the main matrix or other sub matrixes only. Each matrix may be self-aware of it interrogation structure. A condition matrix along with a sub matrix as described above, is shown in FIG. 26. In one embodiment, a sub matrix is identified as "[name@node]". The "name" in the sub matrix name may identify the sub matrix "Type" and the "node" directs to the condition element in the condition matrix.

10. Conditions & Domain-Specific Language (DSL)

In some embodiments, domain-specific language uses a combination of short-hand syntax, comma-separated segments, chemistry identifiers, special "bracket" tests, and keywords to build output sentences.

First and foremost, segment tags may be called in comma-separated order to build from individual tags and associated information the outcome paragraph in a sensible and logical order.

Second, each segment may contain specific instruction about their measurements. In one embodiment, the measurements are called and stored for each panel by its shortest time frame. If in one xml node the panel "CBC" is called in 3 months and later on another condition triggers the same panel "CBC" to be called in 1 month, "1 month" as the shorter time frame may overwrite the "3 months".

Third, in one embodiment, the short hand condition may contain segments only, bracket tests only, or a combination of them along with logic if-then-else statements.

Some examples of Conditions and Domain-Specific Language according to one embodiment of the invention are described below:

a. Chemistries & Bracket Tests:

Bracket tests may look like the following: "[Chemistry!Ca!T3]" or "[eGFRSlope]". The tests are identified by square brackets and have a multi-part syntax within separated by "!". The first example identifies the chemistry "Ca" (calcium) for the latest result over 3 months. "T3" identifies the domain-specific timeframe for 3 months. The second example, like many others, spin off into statistical calculations and other standardized medical interrogations and return the results for display or other short-hand statements (see below).

b. Shorthand & if-then-Else Statements:

In some embodiments, the shorthand definitions utilized chemistry and order form definitions from an enterprise framework along with a simple elements such as "(" ")", "?", ":", ",", "@", or "!" to define logical statements.

Example: "(Ca greater than 5 ? (Ca equal 6 ? ABC1:ABC2):ABC3), ABC4"

In the above example, the syntax reads: If calcium is greater than 5, test if calcium is equal to 6. If this is the case, the segment "ABC1" is added to the outcome report, if not "ABC2" is added. If calcium was not greater than 5, "ABC3" is added. In all cases "ABC4" is added because the segment was outside the if-then-else statement.

All logical statements are separated by commas either within a statement, nested statement, or by simply separating segments.

c. Keywords:

Keywords may define part of the domain-specific language (DSL) and interrogate the chemistry results in a medically sensible fashion. In form of a short-hand syntax the keywords are combined in logical structures to see whether chemistries, order form information, other conditions meet the following keyword conditions. A syntax may look like "(Ca less than 5 ? K1:K3)" or "([Chemistry!Ca!T3] normal ? B2, B3, U2:U3)".

The following shows an excerpt of Litholink's keywords: firsttime (=checks whether the given condition appeared the first time for this patient), greater than, less than, equal, not, unknown (selection or a chemistry level is unknown), yes, no, high, low, normal, last, ever (used in conjunction with other keyword to see whether "ever" high, low, etc.), never, count, slope (slope from linear regression calculation), deltarate (present-last chemistry result over a given time frame, which is defined for each chemistry individually), Delta (present-last), within . . . "T." (used in conjunction with a chemistry), minus (=subtracts to chemistry values from each other before combining with other keywords), CKDStage (guideline-specific stages)

General

The foregoing description of the embodiments of the invention has been presented only for the purpose of illustration and description and is not intended to be exhaustive or to limit the invention to the precise forms disclosed. Numerous modifications and adaptations are apparent to those skilled in the art without departing from the spirit and scope of the invention.

We claim:

1. A method for providing information related to test results, the method comprising:
   receiving, by a processor executing software code, test result data;
   querying, by the processor, standard-of-care data for the test result data using a matrix associated with medical information logic, wherein the medical information logic is extensible apart from compilation of the software code;
   associating, by the processor, in response to the querying, the test result data with the standard-of-care data;
   condensing, by the processor, using medical practice guideline data and the medical information logic, a medical treatment content tag for a specific patient condition;
   accessing, by the processor, the medical treatment content tag for the specific patient condition and a recommended course of action corresponding to the test result data as determined at least in part by the medical treatment content tag;
   building, by the processor, using an embedded language protocol, a patient-specific treatment recommendation using the medical treatment content tag and the recommended course of action; and
   providing, by the processor, a report including the patient-specific treatment recommendation.

2. The method of claim 1, wherein the report comprises a graphical representation of the test result data.

3. The method of claim 1, wherein condensing the medical treatment content tag further comprises determining whether medication is being used.

4. The method of claim 1, wherein the medical information logic comprises linked matrix trees to associate the test result data with standard-of-care data corresponding to the test result data.

5. The method of claim 4, further comprising determining information regarding any change in the test result data from prior test results.

6. The method of claim 4, wherein condensing the medical treatment content tag includes simultaneously interrogating grids of logic within the linked matrix trees for a plurality of diseases.

7. The method of claim 1, wherein condensing the medical treatment content tag further comprises associating at least one of demographic data, medication data, or prior test results with standard-of-care data.

8. The method of claim 1 wherein the test result data is associated with at least one of chronic kidney disease, osteoporosis, or thyroid disease.

9. The method of claim 8 further comprising:
   performing quality control on the test result data; and
   evaluating the test result data in order to identify when at least a portion of the test result data fits into an acceptable range and when at least the portion of the test result data is above or below the acceptable range;
   wherein the report includes information regarding the test result data compared to the acceptable range.

10. The method of claim 1 wherein the condensing the medical treatment content tag further comprises condensing the medical treatment content tag from narrative advice in a set of medical practice guidelines.

11. A system for providing information related to test results, comprising:
    a processor configured to execute software code; and
    a stored data structure communicatively coupled to the processor, the stored data structure defining medical information logic;
    wherein, the processor is further configured to:
    receive test result data;
    query standard-of-care data for the test result data using a matrix associated with medical information logic, wherein the medical information logic is extensible apart from compilation of the software code;
    associate the test result data with standard-of-care data using the medical information logic;
    condense, using medical practice guideline data and the medical information logic, a medical treatment content tag for a specific patient condition;
    access the medical treatment content tag for the specific patient condition and a recommended course of action corresponding to the test result data as determined at least in part by the medical treatment content tag;
    build, using an embedded language protocol, a patient-specific treatment recommendation using the medical treatment content tag and the recommended course of action; and
    provide a report including the patient-specific treatment recommendation.

12. The system of claim 11, wherein the report comprises a graphical representation of the test result data.

13. The system of claim 11, wherein the processor is further configured to determine whether medication is being used to associate the test result data with standard-of-care data to condense the medical treatment content tag.

14. The system of claim 11, wherein the processor is further configured to determine whether the test result data has changed from prior test results.

15. The system of claim 14, wherein the processor is further configured to determine information regarding any change in the test result data from prior test results.

16. The system of claim 11, wherein the processor is further configured to associate at least one of demographic data, medication data, or prior test results with standard-of-care data to condense the medical treatment content tag.

17. The system of claim 11, wherein the test result data are associated with at least one of chronic kidney disease, osteoporosis, or thyroid disease.

18. The system of claim 17, wherein the processor is further configured to:
    perform quality control on the test result data; and
    evaluate the test result data in order to identify when at least a portion of the test result data fits into an acceptable range and when at least the portion of the test result data is above or below the acceptable range;
    wherein the report includes information regarding the test result data compared to the acceptable range.

19. The system of claim 11, wherein the stored data structure further comprises linked matrix trees to simultaneously interrogate grids of logic for a plurality of diseases.

20. The system of claim 11, wherein the processor is further configured to condense the medical treatment content tag from narrative advice in a set of medical practice guidelines.

* * * * *